(12) United States Patent
Orbay et al.

(10) Patent No.: US 9,615,874 B2
(45) Date of Patent: Apr. 11, 2017

(54) BONE PLATE SHAPING SYSTEM

(71) Applicant: Biomet C.V., Gibraltar (GI)

(72) Inventors: Jorge L. Orbay, Coral Gables, FL (US); Javier E. Castaneda, Miami, FL (US); Juergen A. Kortenbach, Miami Springs, FL (US); Robert Sixto, Jr., Miami, FL (US)

(73) Assignee: Biomet C.V., Gibraltar (GI)

( * ) Notice: Subject to any disclaimer, the term of this patent is extended or adjusted under 35 U.S.C. 154(b) by 71 days.

(21) Appl. No.: 14/477,321

(22) Filed: Sep. 4, 2014

(65) Prior Publication Data
US 2015/0045804 A1 Feb. 12, 2015

Related U.S. Application Data

(63) Continuation of application No. 13/075,654, filed on Mar. 30, 2011, now Pat. No. 8,858,562, which is a
(Continued)

(51) Int. Cl.
| | |
|---|---|
| A61B 17/58 | (2006.01) |
| A61B 17/88 | (2006.01) |
| A61B 17/17 | (2006.01) |
| A61B 17/80 | (2006.01) |
| A61B 90/92 | (2016.01) |

(Continued)

(52) U.S. Cl.
CPC ...... *A61B 17/8863* (2013.01); *A61B 17/1728* (2013.01); *A61B 17/80* (2013.01); *A61B 17/8052* (2013.01); *A61B 90/92* (2016.02); *A61B 17/8061* (2013.01); *A61B 17/8085* (2013.01); *A61B 17/888* (2013.01);
(Continued)

(58) Field of Classification Search
CPC ......... A61B 17/88; A61B 17/56; A61B 17/80; A61B 17/1728; A61B 17/7059; A61B 17/8057; A61B 17/8863; A61B 17/8052; A61B 17/8085; A61B 17/8004; A61B 17/8014; A61B 17/8019; A61B 17/808; A61B 17/8866
USPC . 606/101, 86 R, 289, 280, 70, 71, 281–285, 606/290, 104
See application file for complete search history.

(56) References Cited

U.S. PATENT DOCUMENTS

| | | |
|---|---|---|
| 1,105,105 A | 7/1914 | Sherman |
| 1,326,907 A | 1/1920 | Bond |
| | (Continued) | |

FOREIGN PATENT DOCUMENTS

| | | |
|---|---|---|
| AU | 20027914 | 3/2001 |
| CH | 373516 | 11/1963 |
| | (Continued) | |

OTHER PUBLICATIONS

The Titanium Distal Radius Plate Technique Guide; Synthes, 1996.
(Continued)

*Primary Examiner* — Eduardo C Robert
*Assistant Examiner* — Tara R Carter
(74) *Attorney, Agent, or Firm* — Schwegman Lundberg & Woessner, P.A.

(57) ABSTRACT

Methods and systems for bone plate bending are provided which include bending tools that couple relative to the bone plate to bend the plate. Such system permit bending without necessitating that the bending tools are in direct contact with the holes in the plate, which could deform the holes.

36 Claims, 18 Drawing Sheets

Related U.S. Application Data continuation of application No. 11/459,824, filed on Jul. 25, 2006, now Pat. No. 7,935,126, which is a continuation-in-part of application No. 11/384,841, filed on Mar. 20, 2006, now Pat. No. 7,771,433.

(51) Int. Cl.
   *A61B 17/56* (2006.01)
   *A61B 90/00* (2016.01)

(52) U.S. Cl.
   CPC ..... *A61B 17/8888* (2013.01); *A61B 2017/564* (2013.01); *A61B 2090/062* (2016.02)

(56) References Cited

U.S. PATENT DOCUMENTS

| | | |
|---|---|---|
| 2,406,832 A | 9/1946 | Hardinge |
| 2,443,363 A | 6/1948 | Townsend et al. |
| 2,494,229 A | 1/1950 | Collison |
| 2,500,370 A | 3/1950 | McKibbin |
| 3,289,290 A | 12/1966 | Sandor |
| 3,673,378 A | 6/1972 | Kesling |
| 3,713,221 A | 1/1973 | Malmin |
| 3,741,205 A | 6/1973 | Markilf et al. |
| 3,824,834 A | 7/1974 | Durham |
| 3,842,825 A | 10/1974 | Wagner |
| 3,874,808 A | 4/1975 | Zaccardelli et al. |
| 4,304,117 A | 12/1981 | Rawson |
| 4,364,382 A | 12/1982 | Mennen |
| 4,493,317 A | 1/1985 | Klaue |
| 4,565,193 A | 1/1986 | Streli |
| 4,683,878 A | 8/1987 | Carter |
| 4,740,117 A | 4/1988 | Schaff Deleury et al. |
| 4,867,144 A | 9/1989 | Karas et al. |
| 4,889,110 A | 12/1989 | Galline et al. |
| 4,905,680 A | 3/1990 | Tunc |
| 4,955,886 A | 9/1990 | Pawluk |
| 4,957,497 A | 9/1990 | Hoogland et al. |
| 5,002,544 A | 3/1991 | Klaue et al. |
| 5,015,248 A | 5/1991 | Burstein et al. |
| 5,022,277 A | 6/1991 | Shaffer |
| 5,053,036 A | 10/1991 | Perren et al. |
| 5,139,497 A | 8/1992 | Tilghman et al. |
| 5,151,103 A | 9/1992 | Tepic et al. |
| 5,161,404 A | 11/1992 | Hayes |
| 5,190,544 A | 3/1993 | Chapman et al. |
| 5,197,966 A | 3/1993 | Sommerkamp |
| 5,201,737 A | 4/1993 | Leibinger et al. |
| 5,269,784 A | 12/1993 | Mast |
| 5,290,288 A | 3/1994 | Vignaud et al. |
| 5,304,180 A | 4/1994 | Slocum |
| 5,336,224 A | 8/1994 | Selman |
| 5,360,448 A | 11/1994 | Thramann |
| 5,364,398 A | 11/1994 | Chapman et al. |
| 5,366,326 A | 11/1994 | Converse |
| 5,372,598 A | 12/1994 | Luhr et al. |
| 5,413,577 A | 5/1995 | Pollock |
| 5,423,826 A | 6/1995 | Coates et al. |
| 5,474,553 A | 12/1995 | Baumgart |
| 5,487,743 A | 1/1996 | Laurain et al. |
| 5,507,801 A | 4/1996 | Gisin et al. |
| 5,509,933 A | 4/1996 | Davidson et al. |
| 5,558,674 A | 9/1996 | Heggeness et al. |
| 5,564,302 A | 10/1996 | Watrous |
| 5,578,036 A | 11/1996 | Stone et al. |
| 5,586,985 A | 12/1996 | Putnam et al. |
| 5,601,553 A | 2/1997 | Trebing et al. |
| 5,634,927 A | 6/1997 | Houston et al. |
| D383,841 S | 9/1997 | Runciman |
| 5,693,055 A | 12/1997 | Zahiri et al. |
| 5,718,705 A | 2/1998 | Sammarco |
| 5,746,742 A | 5/1998 | Runciman et al. |
| 5,752,958 A | 5/1998 | Wellisz |
| 5,779,706 A | 7/1998 | Tschakaloff |
| 5,785,712 A | 7/1998 | Runciman et al. |
| 5,800,168 A | 9/1998 | Cascione et al. |
| 5,807,396 A | 9/1998 | Raveh |
| 5,851,207 A | 12/1998 | Cesarone |
| 5,888,034 A | 3/1999 | Greenberg |
| 5,935,128 A | 8/1999 | Carter et al. |
| 5,954,722 A | 9/1999 | Bono |
| 5,984,925 A | 11/1999 | Apgar |
| 5,993,449 A | 11/1999 | Schlapfer et al. |
| 6,001,099 A | 12/1999 | Huebner |
| 6,007,535 A | 12/1999 | Rayhack et al. |
| 6,066,142 A | 5/2000 | Serbousek et al. |
| 6,077,271 A | 6/2000 | Huebner et al. |
| 6,123,709 A | 9/2000 | Jones |
| 6,129,730 A | 10/2000 | Bono et al. |
| 6,162,243 A | 12/2000 | Gray et al. |
| 6,162,253 A | 12/2000 | Conzemius et al. |
| 6,170,803 B1 | 1/2001 | Liberfarb |
| 6,193,721 B1 | 2/2001 | Michelson |
| 6,235,034 B1 | 5/2001 | Bray |
| 6,283,973 B1 | 9/2001 | Hubbard et al. |
| 6,306,139 B1 | 10/2001 | Fuentes |
| 6,306,171 B1 | 10/2001 | Conzemius |
| 6,325,803 B1 | 12/2001 | Schumacher et al. |
| 6,332,887 B1 | 12/2001 | Knox |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,416,518 B1 | 7/2002 | DeMayo |
| 6,436,103 B1 | 8/2002 | Suddaby |
| 6,506,191 B1 | 1/2003 | Joos |
| 6,587,750 B2 | 7/2003 | Gerbi et al. |
| 6,602,255 B1 | 8/2003 | Campbell et al. |
| 6,623,486 B1 | 9/2003 | Weaver et al. |
| 6,656,181 B2 | 12/2003 | Dixon et al. |
| 6,663,632 B1 | 12/2003 | Frigg |
| 6,695,845 B2 | 2/2004 | Dixon et al. |
| 6,712,818 B1 | 3/2004 | Michelson |
| 6,730,091 B1 | 5/2004 | Pfefferle et al. |
| 6,821,278 B2 | 11/2004 | Frigg et al. |
| 6,866,665 B2 | 3/2005 | Orbay |
| 6,928,733 B2 | 8/2005 | Rubbert et al. |
| 6,960,211 B1 | 11/2005 | Pfefferle et al. |
| 7,048,477 B2 | 5/2006 | Abrams |
| 7,090,676 B2 | 8/2006 | Huebner et al. |
| 7,128,744 B2 | 10/2006 | Weaver et al. |
| 7,179,260 B2 | 2/2007 | Gerlach et al. |
| 7,189,237 B2 | 3/2007 | Huebner |
| 7,229,446 B2 | 6/2007 | Capanni |
| 7,273,481 B2 | 9/2007 | Lombardo et al. |
| 7,357,804 B2 | 4/2008 | Binder et al. |
| 7,473,257 B2 | 1/2009 | Knopfle et al. |
| 7,578,825 B2 | 8/2009 | Huebner |
| 7,740,634 B2 | 6/2010 | Orbay et al. |
| 7,771,433 B2 | 8/2010 | Orbay et al. |
| 7,935,126 B2 | 5/2011 | Orbay et al. |
| 8,858,562 B2 | 10/2014 | Orbay et al. |
| 2001/0037156 A1 | 11/2001 | Burstein et al. |
| 2002/0032446 A1 | 3/2002 | Orbay |
| 2002/0042654 A1 | 4/2002 | Masini |
| 2002/0045897 A1 | 4/2002 | Dixon et al. |
| 2002/0147450 A1 | 10/2002 | LeHuec et al. |
| 2002/0156474 A1 | 10/2002 | Wack et al. |
| 2003/0040753 A1 | 2/2003 | Daum et al. |
| 2003/0083667 A1 | 5/2003 | Ralph et al. |
| 2003/0171754 A1 | 9/2003 | Del Medico |
| 2003/0225411 A1 | 12/2003 | Miller |
| 2004/0034356 A1 | 2/2004 | LeHuec et al. |
| 2004/0097937 A1 | 5/2004 | Pike et al. |
| 2004/0102777 A1* | 5/2004 | Huebner ............ A61B 17/1728 606/281 |
| 2004/0102778 A1 | 5/2004 | Huebner et al. |
| 2004/0116930 A1 | 6/2004 | O'Driscoll et al. |
| 2004/0116934 A1 | 6/2004 | Capanni |
| 2004/0176780 A1 | 9/2004 | Knopfle et al. |
| 2004/0186482 A1 | 9/2004 | Kolb et al. |
| 2004/0219479 A1 | 11/2004 | Malin et al. |
| 2005/0011659 A1 | 1/2005 | Tempelman et al. |
| 2005/0028398 A1 | 2/2005 | Jacobson |

(56) References Cited

U.S. PATENT DOCUMENTS

| | | |
|---|---|---|
| 2005/0049594 A1 | 3/2005 | Wack et al. |
| 2005/0049710 A1 | 3/2005 | O'Driscoll et al. |
| 2005/0086939 A1 | 4/2005 | Schmid |
| 2005/0090825 A1 | 4/2005 | Pfefferle et al. |
| 2005/0101961 A1 | 5/2005 | Huebner et al. |
| 2005/0165401 A1 | 7/2005 | Pack |
| 2005/0182406 A1 | 8/2005 | Orbay et al. |
| 2005/0187552 A1 | 8/2005 | Michelson |
| 2005/0216090 A1 | 9/2005 | O'Driscoll et al. |
| 2005/0234467 A1 | 10/2005 | Rains |
| 2005/0261688 A1 | 11/2005 | Grady, Jr. et al. |
| 2006/0089648 A1 | 4/2006 | Masini |
| 2006/0149265 A1 | 7/2006 | James et al. |
| 2006/0161158 A1 | 7/2006 | Orbay et al. |
| 2006/0173459 A1 | 8/2006 | Kay et al. |
| 2006/0195104 A1 | 8/2006 | Schlafli et al. |
| 2006/0200145 A1 | 9/2006 | Kay et al. |
| 2006/0264949 A1 | 11/2006 | Kohut et al. |
| 2007/0225714 A1 | 9/2007 | Gradl |
| 2007/0233111 A1 | 10/2007 | Orbay et al. |
| 2008/0009951 A1 | 1/2008 | Hodge |
| 2015/0148850 A1 | 5/2015 | Orbay et al. |

FOREIGN PATENT DOCUMENTS

| | | |
|---|---|---|
| DE | 19936061 | 3/2000 |
| DE | 10015734 | 9/2001 |
| EP | 0471419 | 2/1992 |
| EP | 1836982 | 9/2007 |
| FR | 2367479 | 5/1978 |
| JP | 2003-102743 | 4/2003 |
| WO | WO99/05968 | 2/1999 |
| WO | WO01/91660 | 12/2001 |
| WO | WO03/007832 | 1/2003 |
| WO | WO2004/024009 | 3/2004 |
| WO | WO2004/045455 | 6/2004 |
| WO | WO2004/084701 | 10/2004 |
| WO | WO2005020851 | 3/2005 |
| WO | WO2005023127 | 3/2005 |
| WO | WO2006065512 | 6/2006 |

OTHER PUBLICATIONS

The Distal Radius Plate Instrument and Implant Set Technique Guide; Synthes, 1995.

SCS/V Distal Radius Plate Volar; Avanta; 1998.

SCS/D Distal Radius Plate System; Avanta; 1997.

Sumary of Safety and Effectiveness Information; Synthes (USA); 1998.

Hand Innovations, DVR Anatomic Plate with F.A.S.T. Guide Technology, DVR Anatomic The Proven Standard in Volar Plating, on sale as of Mar. 2005.

U.S. Appl. No. 11/011,917, filed Dec. 14, 2004, Applicant: Javier E. Castaneda et al.

U.S. Appl. No. 12/977,705, filed Dec. 23, 2010, Applicant: Javier E. Castaneda et al.

U.S. Appl. No. 12/818,467, filed Jun. 18, 2010, Applicant: Jorge L. Orbay et al.

U.S. Appl. No. 12/977,729, filed Dec. 23, 2010, Applicant: Javier E. Castaneda et al.

Graduated Stability Plates (GSP); Stryker Corporation; 2004.

"U.S. Appl. No. 14/614,034, Non Final Office Action mailed Jul. 11, 2016", 10 pgs.

* cited by examiner

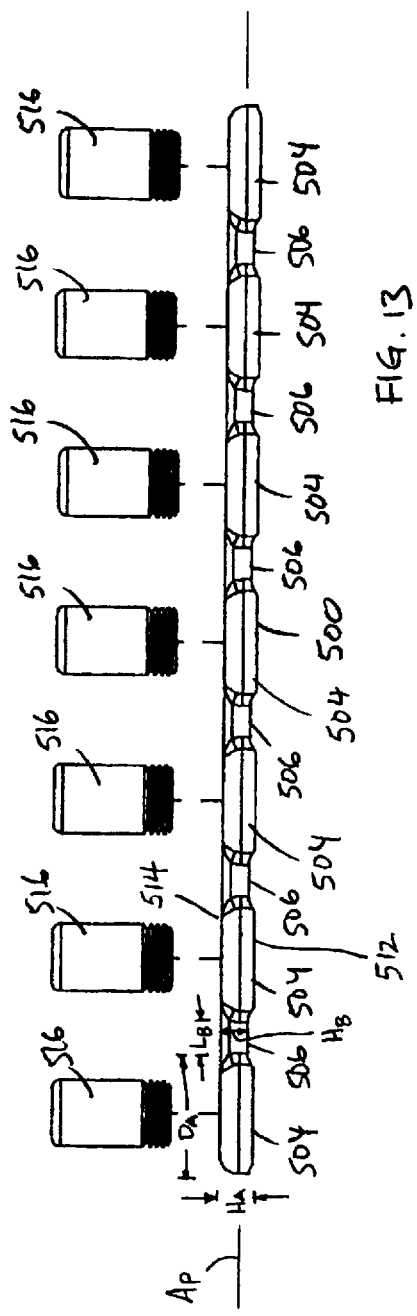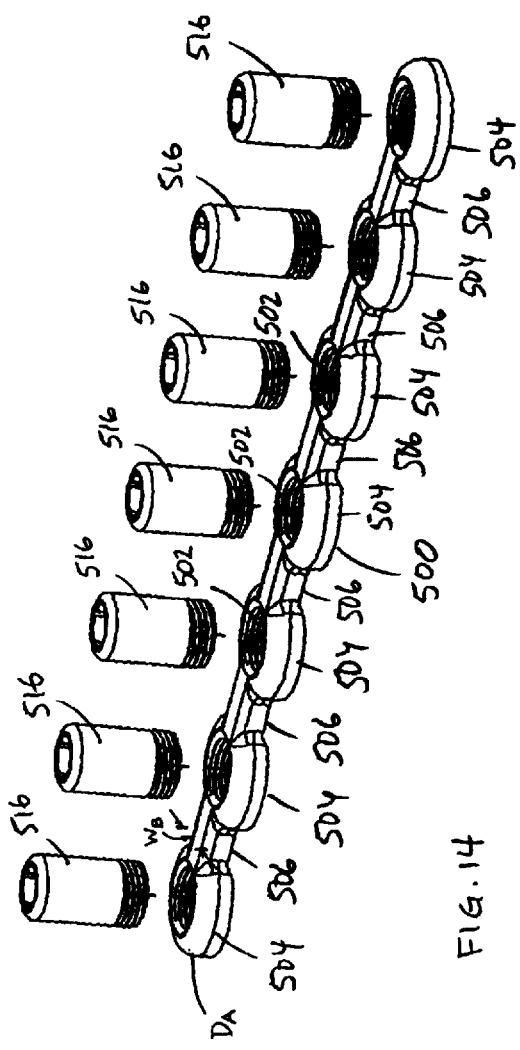

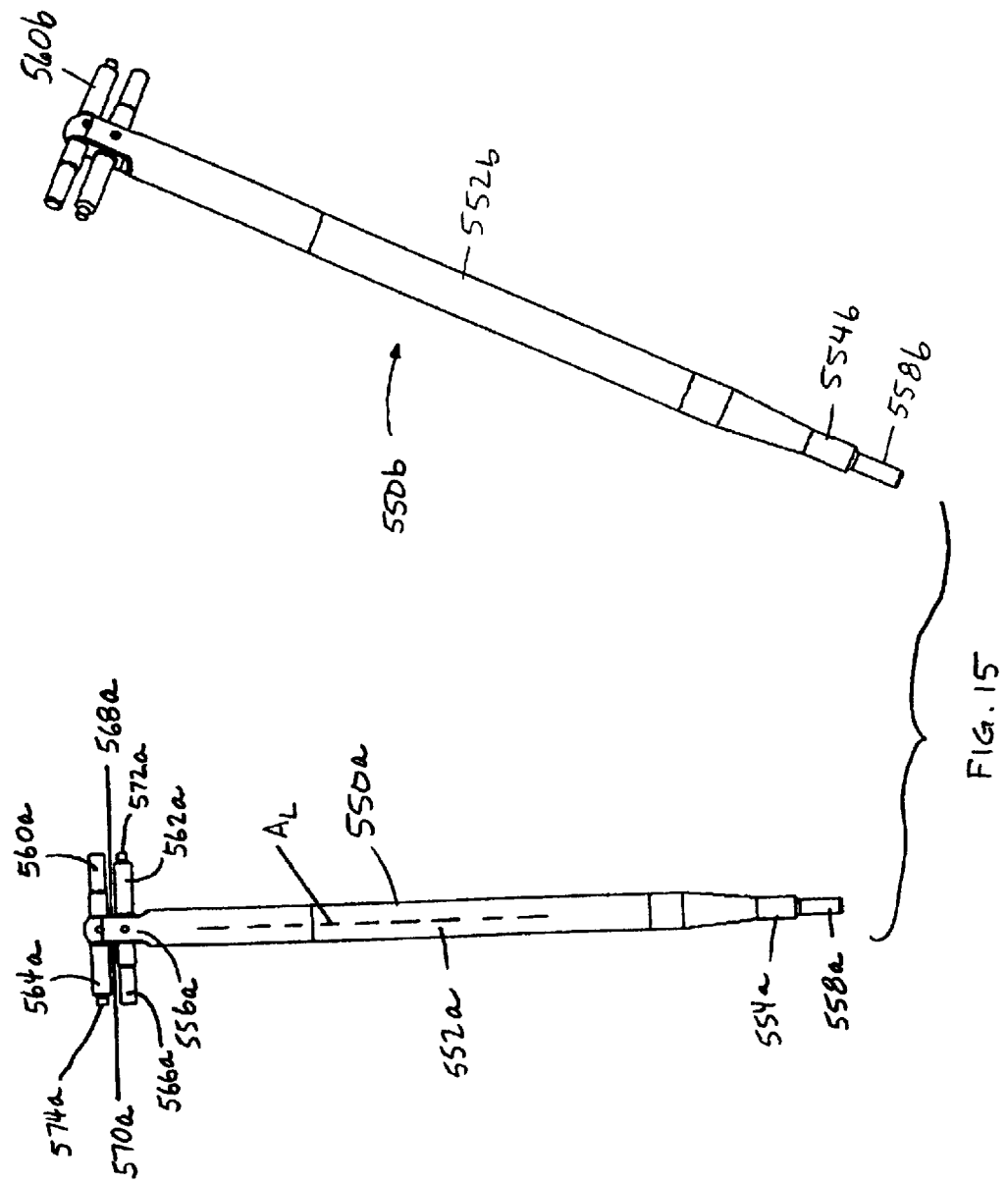

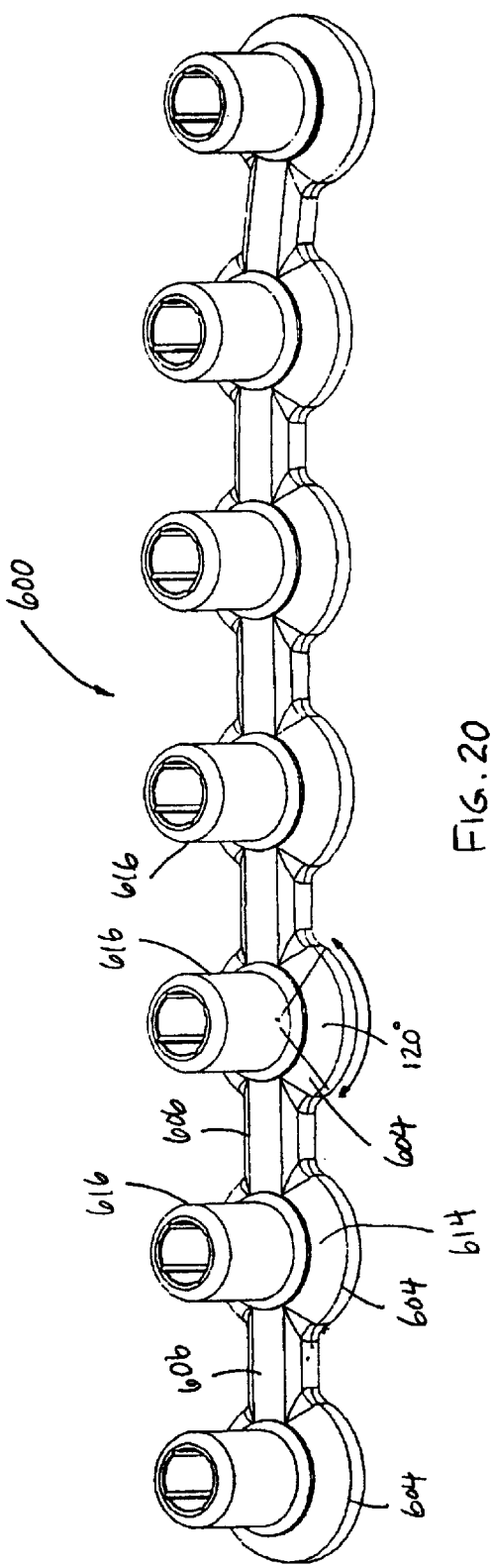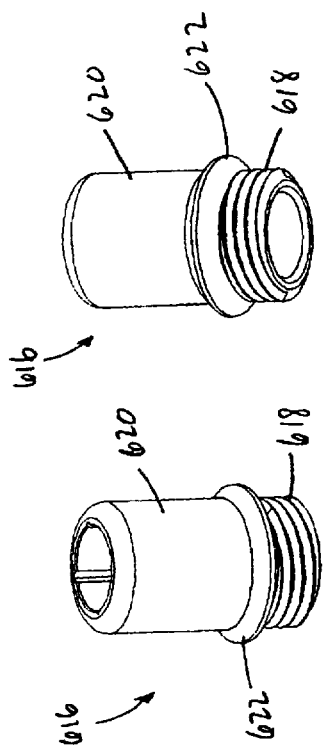
FIG. 20
FIG. 21
FIG. 22

BONE PLATE SHAPING SYSTEM

CROSS-REFERENCE TO RELATED APPLICATIONS

This application is a continuation of U.S. Ser. No. 13/075,654, filed Mar. 30, 2011, which is a continuation of U.S. Ser. No. 11/459,824, filed Jul. 25, 2006, now issued as U.S. Pat. No. 7,935,126, which is a continuation-in-part of U.S. Ser. No. 11/384,841, filed Mar. 20, 2006, now issued as U.S. Pat. No. 7,771,433, all of which are hereby incorporated by reference herein in their entireties.

BACKGROUND OF THE INVENTION

Field of the Invention

This invention relates broadly to surgical devices. More particularly, this invention relates to orthopedic implants, and specifically to elements to implant and shape a bone plate.

State of the Art

Alignment and fixation of a fracture are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic.

Plating utilizes a stabilizing metal plate typically placed against the bone, fixed-angle fasteners (which may have threaded or non-threaded shafts) positioned through the plate and entering drilled holes adjacent an articular bone surface, and cortical screws extending from the plate into holes drilled in the bone to provide stabilized fracture fixation. For example, co-owned U.S. Pub. No. 20040193164 A1 to Orbay, which is hereby incorporated by reference herein in its entirety, discloses a plate particularly adapted to treat dorsally displaced metaphyseal fractures from the volar side of the wrist.

When fixed-angle fasteners are utilized in conjunction with a bone plate, it is necessary to ensure that the pilot holes drilled for the fasteners are co-axial with the hole axes. Otherwise, the shaft of the fasteners will not properly align with the anatomy, and the head of the fasteners will not properly align with the threaded holes of the plate, potentially resulting in cross-threading. As a result, with the plate placed upon the bone, prior to drilling each hole in the bone in alignment with a threaded hole, a drill guide is attached to the plate at the threaded hole. The guide defines a tubular passage which directs the drill bit in the proper orientation for a fastener through the particular threaded hole. After drilling each hole, the drill guide is removed, the fastener is inserted in the threaded hole, and the drill guide is coupled to a subsequent threaded hole.

The process of attaching the drill guide during the surgical procedure is laborious. It can be difficult to locate the appropriate angle for threadably coupling the guide to the peg hole during the procedure, given that each threaded hole may have a discrete axis angle from the other threaded holes. Such difficulty can unnecessarily prolong the surgical procedure.

Fragment plates are commonly used to fixate fractures along a bone, e.g., along the diaphysis or at specific diaphyseal-metaphyseal or metaphyseal locations. Such plates are generally elongate, L-shaped, Y-shaped or have another shape which is suited for placement on a portion of a bone. The plates can be of varying length depending upon the intended fixation application. When fragment plates are provided with threaded holes they are subject to the same practical labor intensity for use as presented above with respect to the volar plate; i.e., it is laborious to attach a drill guide at each threaded hole for drilling a hole in alignment with the axis of the hole for receiving the fixed angle fastener therethrough.

In addition, the anatomy for which the fragment plates are designed often differs from the exact contours of the bone contacting surfaces of the plates. Some fragment plates have been designed to be shaped away from the bone for a better anatomical fit. However, presently available plating systems are not well adapted for in situ reconfiguration. Therefore, it has been necessary to shape a plate off the target bone with bending tools, remove the bending tools, place the plate in position on the bone to which the plate will eventually be attached, approximate the additional amount of reconfiguring required, remove the plate, and repeat the process until the plate approximately conforms to the shape of the bone. Moreover, in order to best fit the anatomy a plate may need to be re-contoured along three axes, and it has been difficult to transfer the contours of the anatomy to a stiff metal plate, especially when such reshaping is done at a distance from the bone.

Moreover, the problems with shaping a plate are compounded when the plate has threaded holes for receiving fasteners. In distinction from non-fixed angle fragment plates, inserting bending tools into the threaded holes of the plate and applying a force to the plate with the bending tools may distort the threads making such holes unaccepting to their threaded fasteners.

SUMMARY OF THE INVENTION

It is therefore an object of the invention to facilitate the drilling of holes in bone in alignment with the threaded holes in a bone plate.

It is another object of the invention to obviate the difficulties presented in connecting a drill guide in alignment with a threaded fixed angle hole in a bone plate at the time of surgery.

It is also an object of the invention to provide a system to reshape a plate while the plate is located on the bone.

It is a further object of the invention to provide a system which permits reshaping of the plate in three dimensions.

It is yet another object of the invention to provide a system which protects the threads of fixed angle holes during plate reshaping.

In accord with these objects, which will be discussed in detail below, drill guide tips are pre-assembled into at least one and preferably each of the threaded holes of the plate, so that the surgeon does not have to thread the drill guide with the plate positioned on the bone. The pre-assembly can be done by the operating room technician or at the factory. The drill guide tips may be reusable or disposable. The tips are sufficiently short that they do not interfere with adjacent tips or adjacent structure on the plate or intended to be inserted through the plate.

In a preferred method of pre-assembling the tips to the plate, a nest of short pins is placed beneath the plate such that the pins extend through the holes in the plate along the same angles as the axes of the holes. The pins then guide the tips to be threaded into the holes at the correct angle. Alternatively, no nest is utilized and the tips are individually guided into the holes at the appropriate angle. With respect to a fragment plate, such angle is typically normal to the bone contacting surface of the plate.

There are two options for using the tips as drill guides. One is to attach a drill guide extension. The tip and extension together function as a conventional drill guide. After drilling, the extension is used to remove the tip from the plate. According to another use, the tip is used as a guide for a drill bit without any additional extension and then removed with a separate tool.

In addition, the guide tips have purpose other than for guiding a drill. The guide tips can also be used in conjunction with plate bending tools, and are particularly advantageous when the guide tips are pre-assembled on a fragment plate having a plurality of spaced apart fixed angle holes separated by a plate portion which can be deformed under force. Preferably two bending tools are used together to bend the plate, and the bending tools have first and second ends which are at least partially inserted into guide tips in two holes in the plate. Torque is applied by coupling the first ends of each of the tools to the guide tips inserted in threaded holes and manipulating the tools, lateral bending forces (i.e., bending within the plane of the plate) are applied with the second ends in the guide tips, and longitudinal bending forces are applied with the first ends or a combination of the first and second ends in the guide tips. The bending tools can be operated and forces can be applied to reshape the plate with the plate positioned directly on the bone to reshape the plate in close conformance to the bone surface. As the plate is shaped at each set of two holes, bending tools are removed and the guide tips can be used as discussed above as drill guides to drill holes into bone beneath that portion of the plate. Fixed angle screws are then used to couple that portion of the fragment plate to the bone. The adjacent portion of the plate is then shaped and fixed to the bone in a like manner with the process repeated until the entire plate is shaped and coupled to the bone.

Additional objects and advantages of the invention will become apparent to those skilled in the art upon reference to the detailed description taken in conjunction with the provided figures.

BRIEF DESCRIPTION OF THE DRAWINGS

FIG. 13 is an exploded side elevation view of a fragment plate with guide tips;

FIG. 14 is an exploded perspective view of the fragment plate and guide tips of FIG. 13;

FIG. 15 is a set of benders, shown in side elevation and perspective view;

FIG. 20 is a perspective view of a fragment plate provided with another embodiment of a guide tip;

FIG. 21 is a top perspective view of the guide tip shown on the plate in FIG. 20;

FIG. 22 is a bottom perspective view of the guide tip shown on the plate in FIG. 20;

DETAILED DESCRIPTION

Figure 1:
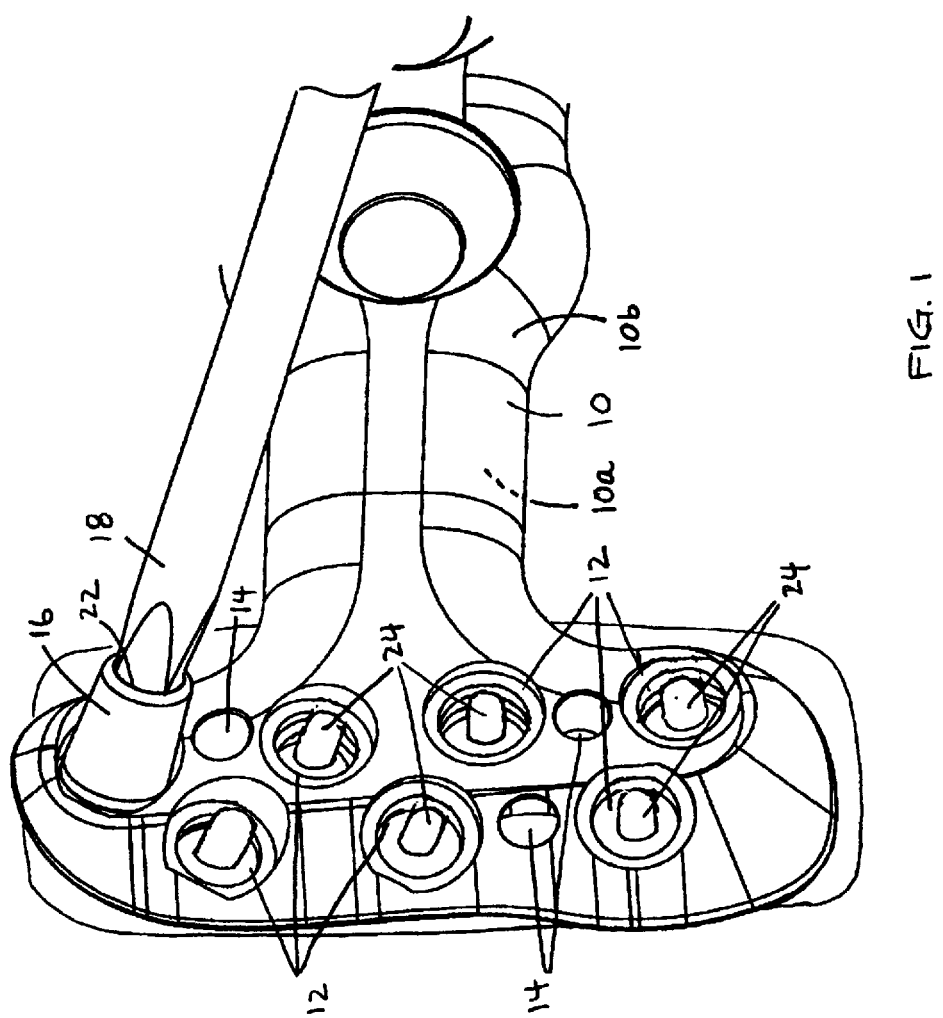
FIG. 1 is a perspective view of a bone plate and a drill guide tip being inserted or removed from the plate with a tool.

Turning now to FIG. 1, a bone plate 10 is shown. The bone plate 10, and all plates described herein, includes inner or lower (bone-facing) and outer or upper (bone-opposing) surfaces 10a, 10b. One or both of these surfaces may be contoured generally to follow a surface of a target bone (or bones) for which the bone plate is intended, so that the bone plate maintains a low profile and fits onto the bone(s). For example, the inner surface 10a of the plate may be generally complementary in contour to the bone surface. The outer surface 10b may correspond in contour to the bone surface and may be generally complementary to the inner surface of the plate.

Figure 2:
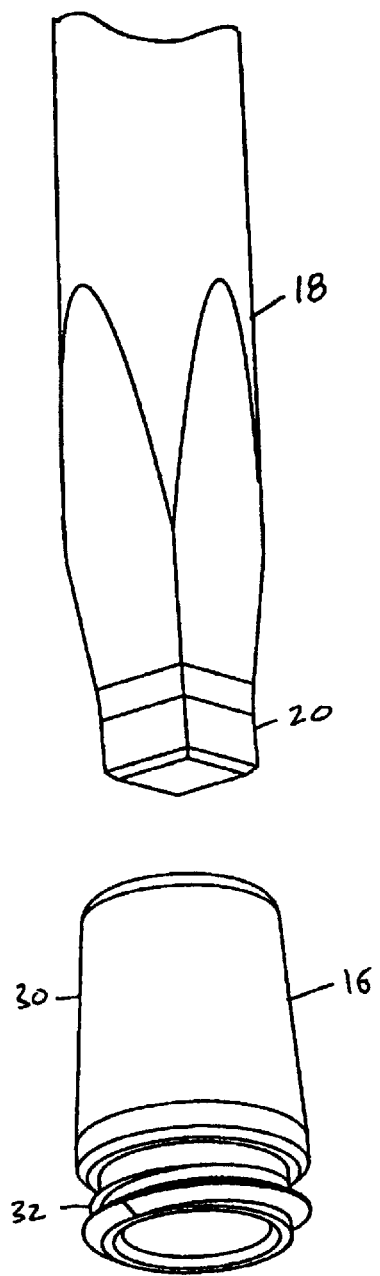
FIG. 2 is an exploded perspective view of drill guide tip and tool.

Bone plate 10 shown is particularly for placement over the volar side of the distal radius. The bone plate 10 includes a plurality of threaded peg holes 12 for threadably receiving the heads of pegs or locking screws (not shown) therein and relatively smaller alignment holes 14 sized to closely receive K-wires in a fixed angle orientation. In a preferred bone plate, the axes of the peg holes are all oblique relative to each other. In one of the peg holes, a drill guide tip 16 is shown being pre-assembled into the hole with an insertion tool 18. Referring to FIGS. 1 and 2, in a preferred embodiment, the engagement between the insertion tool 18 and tip 16 is a tapered square 20 engaging a circular opening 22, with the edges of the square driver providing sufficient frictional force to rotate the tip into and out of engagement with the plate 10. Other suitable engagements may be used as well.

Pre-assembly of the tips 16 into the peg holes of the plate 10 is preferably performed so that the surgeon does not have to thread the drill guide tips 16 with the plate once the plate 10 is positioned on the bone during the procedure. The pre-assembly can be done by the operating room technician or at the factory. In a preferred method of pre-assembly, a nest of short pins 24 is placed beneath the plate such that the pins extend through the holes in the plate along the same angles as the axes of the holes. The pins 24 then guide the tips to be threaded into the holes at the correct angle. With respect to a fragment plate, such angle is typically normal to the bone contacting surface of the plate. The pins 24 and insertion tool 18 are sized such that they do not interfere with each other. Alternatively, no nest is utilized and the tips 16 are individually guided into the holes at the appropriate angle. The drill guide tips 16 may be reusable or disposable.

Figure 3:
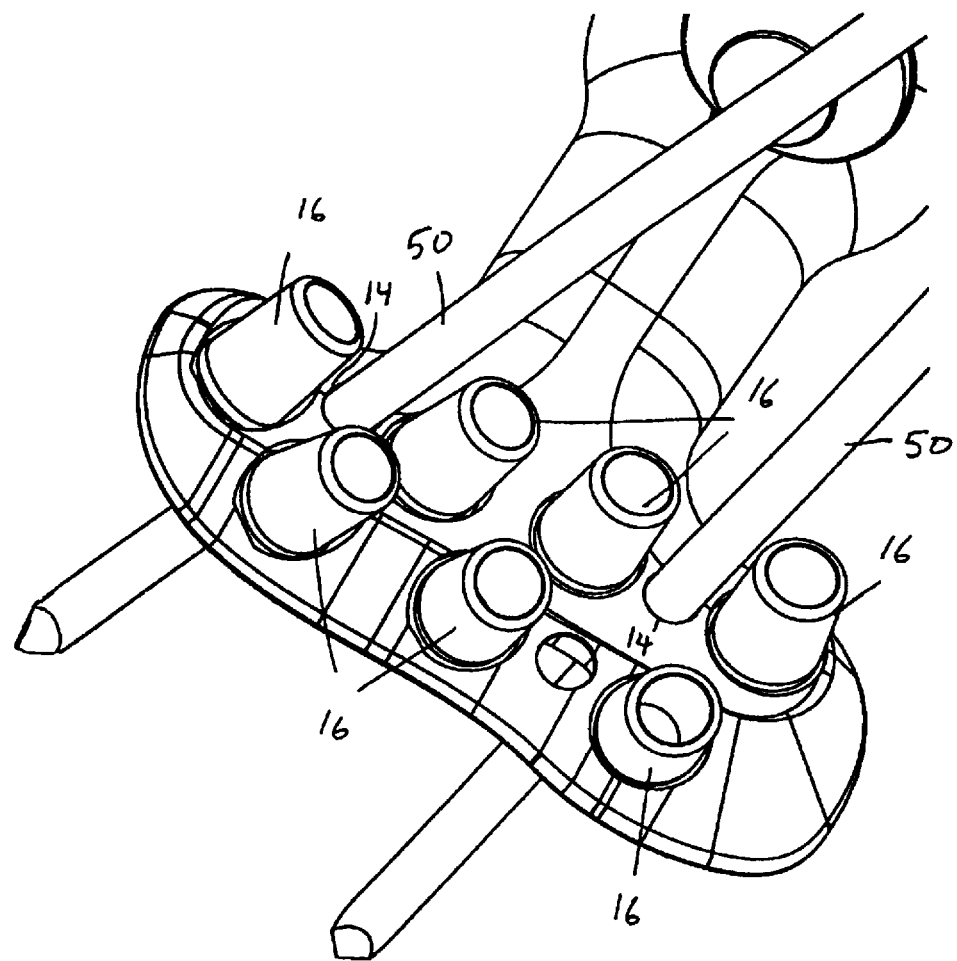
FIG. 3 is a perspective view of the bone plate loaded with drill guide tips and K-wires.

Referring to FIGS. 2 and 3, the tips 16 have a frustoconically tapered upper portion 30 and lower threaded portion 32, and are sufficiently short so that they do not interfere with adjacent tips, adjacent structure on the plate, or structure intended to be inserted through the plate, e.g., K-wires 50 through alignment holes 14. Alternatively, the upper portion 30 may be cylindrical. The lower threaded portion 32 of the tips does not have to be as long as conventional drill guides, as the threading into the plate is done away from the surgical environment under easier conditions, whether at the factory (best case) or pre-implantation at the medical facility. Shortening the threaded portion reduces protrusion of the guide tip below the plate relative to convention drill guides, allowing the plate 10 to sit closer to the bone while drilling, as discussed further below.

The drill guide tips also eliminate the need to "countersink" holes for a drill guide for the distal row of holes in a distal radius plate. More particularly and for the following reasons, in the prior art it is initially necessary to drill holes in bone through the distal row of threaded peg holes with a drill bit larger than the diameter of the peg shaft which will eventually be inserted through the peg holes. The plate is very thin at the distal row. The prior art drill guide has a "nose" section which is cylindrical and unthreaded and approximately 0.030" long, which is slightly longer than the pitch of the peg-hole thread (0.023"). The nose section diameter is just under the inner diameter of thread so that it guides itself with one full turn of the thread and establishes the direction of the hole before the threads are engaged. If the plate thread depth is very small (as is the case for distal holes) there is no room below the plate for the nose section of the drill guide because the bone blocks entry. Thus, countersink holes must be drilled.

Figure 4:
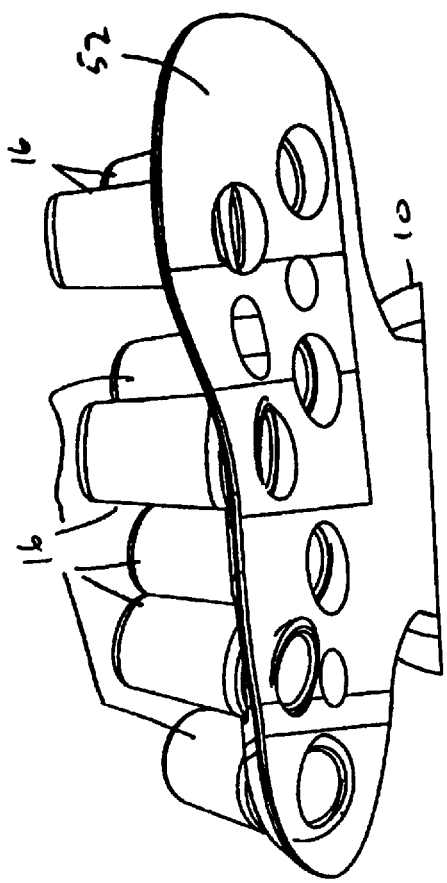
FIG. 4 is a front end view of a head portion of the plate showing that the drill guide tips do not protrude through the bottom surface of the plate.

In accord with the invention, the drill guide tips do not require a "nose" section since they will be assembled with some other guidance (e.g., the above described nest of pins 24) or freehand. The drill guide tips can be made very short since they need just to hold on to the threads of the peg holes of a distal radius plate. One and one-half threads of engagement has been shown to provide a satisfactory coupling of the tip to the plate, and referring to FIG. 4 provides that the drill guide tip 16 does not protrude through the bottom 52 of the plate 10. In addition to eliminating the requirement for countersinking, the fact that drill guide tips are so short results in the plate seating almost completely flush on the bone. Furthermore, the cylindrical unthreaded nose portion of the conventional drill guide, whose only job is to help the surgeon find by feel the current angle of the peg hole, is not required. A preferred size for each tip is preferably approximately 0.150-0.250 inch in length and certainly less than one inch. As such, the tip extends a short distance (maximum one inch and preferably not more than 0.25 inch) above the upper surface (the surface opposite the bone contacting surface) of the plate.

There are two options for using the tips as drill guides. According to a first option, the tips 16 are used as the sole guide for a drill bit and then removed with a tool similar to the insertion tool 18. The length of the tips provides sufficient guidance for the drill bit. In this use, the inner surface of the tip is preferably hard, e.g., metal. Thus, the tips 16 may be made entirely of metal or have an outer plastic body with an insert molded metal tube, e.g. hypotube, which is hard and readily available with thin walls.

Figure 5:
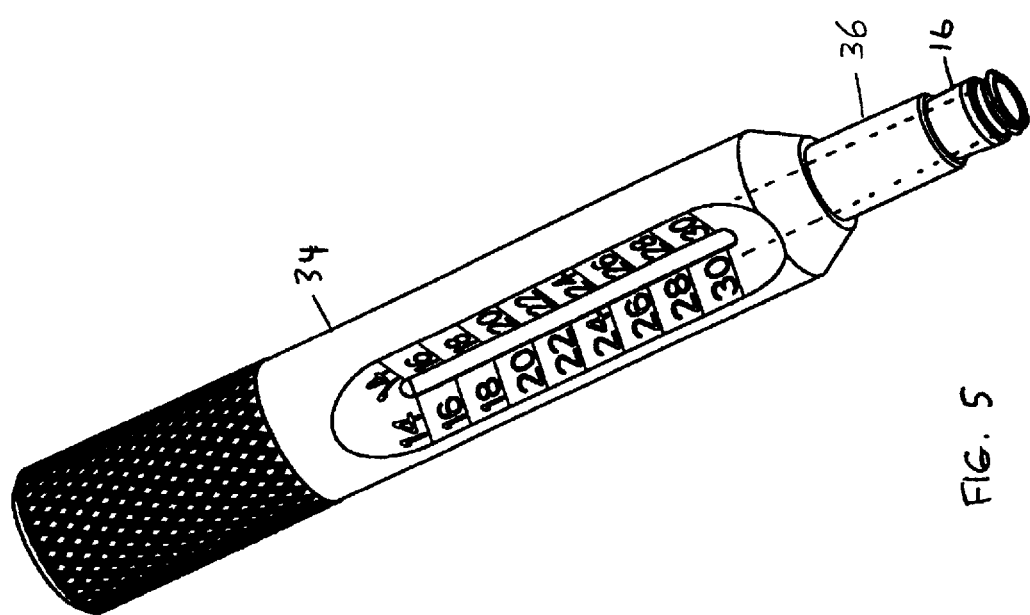
FIG. 5 is a perspective view of a drill guide tip and drill guide extension.

Referring to FIG. 5 and according to a second option, a drill guide extension 34 may be attached to the top of the tip 16. The tip 16 and extension 34 together function as a full length drill guide. The engagement between the drill guide extension 34 over the tip 16 is preferably such that a continuous constant diameter path is provided through the interiors of the extension and tip. To that end, the end 36 of the extension 34 is preferably stepped to fit the upper portion of the tip. The surgeon drills through the drill guide extension and tip, thereby taking advantage of the longer guidance which may be used in conjunction with a scale and/or gauge to measure the depth of the drilled hole for peg length selection. After drilling, the extension 34 and tip 16 are removed from the plate 10, and the extension 34 may also function as a tool for tip 16 removal. In fact, the taper at the upper portion 30 (FIG. 2) of the tip provides a means for axial and frictional engagement by the extension 34 which permits rotational engagement. Once removed from the plate, the tip is then is pulled of the extension by hand or may be dispensed into a container without manual contact.

It is desirable to have some provision within the surgical set to collect the tips for counting as they are removed; i.e., to ensure that all tips from the plate are removed from the surgical site. In order to facilitate collection of the tips, it is desirable that the drill guide tips have a very conspicuous color, e.g., green or blue. If made out of metal, it may be desirable to make them out of titanium or aluminum and anodize them in a bright color that contrasts with the background in the surgical wound and the bone plate. A specialized container may be provided, or a dummy plate with threaded holes may be used to attach the tip thereto.

For drilling through the tips 16 where no drill guide extension is used, it may be desirable to modify the flutes of the drill bit, e.g. shortening and/or increasing twist, to reduce the play within the tip.

Figure 6:
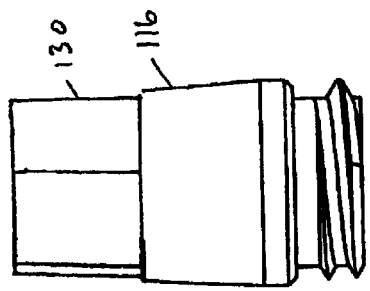
FIG. 6 is a side elevation of a first embodiment of a drill guide tip.
Figure 7:
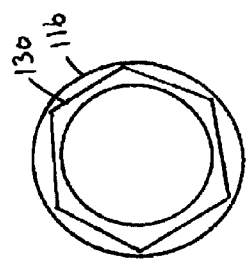
FIG. 7 is a top view of the first embodiment of the drill guide tip.

Other embodiments of the tips and extensions may be provided. For example, referring to FIGS. 6 and 7, the tips 116 may have an upper portion 130 with an exterior hex shape, or any non-circular exterior cross-sectional shape that will facilitate torque transmission. To remove the tip from the plate the surgeon rotates the extension, unthreading the tip.

Figure 9:
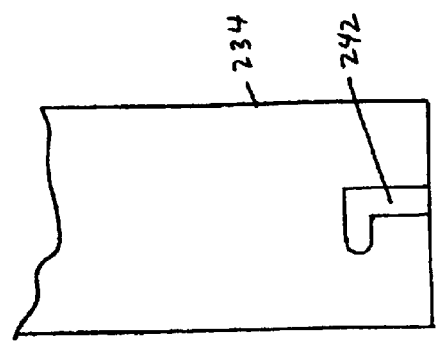
FIG. 9 is a side elevation view of an embodiment of a drill guide extension.
Figure 8:
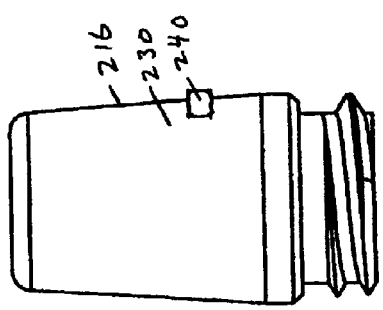
FIG. 8 is a side elevation of a second embodiment of a drill guide tip.

Turning now to FIGS. 8 and 9, according to another embodiment of the invention, the tips 216 may be joined to the extension via one or more lateral protrusions 240 on the body 230 of the tip and corresponding "key slots" 242 in the extension 234.

Figure 10:
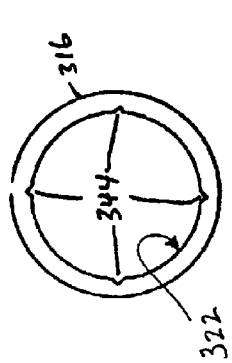
FIG. 10 is a top view of a third embodiment of a drill guide tip.

Referring to FIG. 10, according to a further embodiment of the invention, the tips 316 may be joined to the extension by providing one or more corners 344 to the inner circular opening 322 of the tip, and one or more outer corresponding corners on the extension which frictionally engage in the tip.

Figure 11:
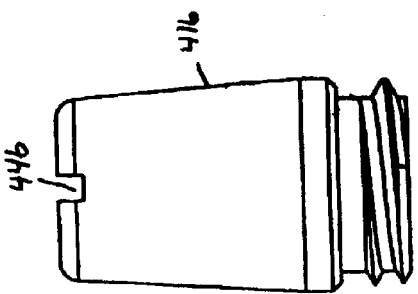
FIG. 11 is a side elevation of a fourth embodiment of a drill guide tip.
Figure 12:
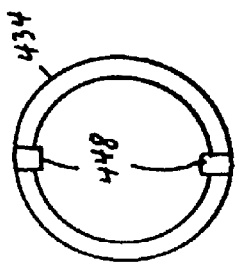
FIG. 12 is a bottom view of an embodiment of a drill guide extension engageable with the drill guide tip of FIG. 11.

Turning to FIGS. 11 and 12, according to another embodiment of the invention, the tips 416 may include upper radially arranged slots 446 (e.g., 180° or 120° separation) and the extension 434 includes corresponding radially arranged pegs 448 which engage the tips 416 at the slots 446.

Turning to FIGS. 13 and 14, the tips can also be used to facilitate bending of a fragment plate 500 in a manner that does not distort the threads at the holes 502 at which the tips 516 are coupled, as described below. The tips 516 are cylindrical having inside corners (similar to corners 344 in FIG. 10) to aid removal and/or extension guide coupling. Such distortion would otherwise prevent the holes 502 from accepting fixed angle fasteners with threaded heads which are later threadably coupled into the threaded holes.

Bendable plates, as described in more detail below, according to the invention may have at least one, and generally two or more, distinct anchor (or bone-attachment) portions including a threaded hole and at which the plate is configured to be secured to bone. Each anchor portion may be structured for a specific portion of a bone, generally to fit against a surface region of a specific or general bone. For example, the bone plate may include a proximal anchor portion for attachment to a more proximal region of a bone, and a distal anchor portion for attachment to a more distal region of the same bone. In some embodiments, the bone plates may include a support (or buttress) portion connected to an anchor portion. The support portion may lack connective features that permit a direct connection of the support portion to the bone with one or more fasteners. Such a support portion may limit movement of a bone fragment using contact between the support portion and the fragment, and may include projections or prongs to engage the fragment more effectively.

The bone plates described herein may be configured for use on any suitable bone of the human body and/or of another vertebrate species. Exemplary bones may include bones of the arms (radius, ulna, humerus), legs (femur, tibia, fibula, patella), hands, feet, the vertebrae, scapulas, pelvic bones, cranial and mandibular bones, the ribs and/or the clavicles, among others.

The fragment plate 500 is generally elongate, preferably designed with a series of alternating round anchor portions 504 and relatively narrower bridge portions 506 that connect the anchor portions together. The anchor portions 504 have a diameter $D_A$ and a height $H_A$, and the bridge portions 506 have a length $L_B$, a width $W_B$, and height $H_B$. By way of example, and not by limitation, the following dimensions are provided for a plate for use on a radius bone: diameter $D_A$=0.22 inch, $H_A$=0.060 inch, $L_B$=0.065 inch, $W_B$=0.085 inch, and $H_B$=0.50 inch. To maintain structural integrity and desired stiffness, while facilitating bendability, the length $L_B$ of each bridge portion is preferably less than one half, and more preferably less than forty percent, of the anchor diameter $D_A$. The plate includes an inner (bone-facing) surface 512 and an outer (bone-opposing) surface 514. In use, a long axis $A_P$ defined through the plate 500 may be aligned with the long axis of a corresponding bone or may extend obliquely or transversely relative to the long axis of the bone. The dimensions of the anchor and bridge portions 504, 506, and the number of anchor and bridge portions, may be varied according to the intended use, for example, to match the plate with a preselected region of bone(s) and/or to a particular injury to the bone. The plates may be generally linear for use on the shaft of a long bone or may have a nonlinear shape, such as for use near an end of a bone. For example, the plate may be generally T-shaped, with a longer axis for attachment to a shaft portion of a bone, and a transverse portion connected to the longer axis portion, to provide a wider platform for attachment near an end of the bone. Also, by way of example, the transverse portion may be of a different construct, e.g., a plate portion without any bridge portions but multiple threaded holes, as shown in FIG. 1. The plate may also be Y-shaped. In some embodiments, each bone plate may be configured for use on both sides of the body, such as when the bone plates are bilaterally symmetrical. In some embodiments, each bone plate may be asymmetrical and configured for use on either the left or the right side of the body.

Threaded holes 502 are provided in the anchor portions 504, and preferably each threaded hole 502 is provided with a guide tip 516. However, the tips may be strategically pre-assembled at locations that are recognized to commonly benefit from contour shaping for the plate 500 depending on the shape of the plate and to best fit on the bone.

Referring to FIG. 15, two preferably identical plate benders (shaping tools) 550a, 550b have ends which can be coupled to the tips 516 and can be used alone or together to contour the plate 500 (FIGS. 13 and 14). As described in more detail below, the benders 550a, 550b and tips 516 permit such plate contouring to occur with the plate 500 positioned directly on the bone. Each tool, described with respect to tool 550a, includes a handle portion 552a and first and second ends 554a, 556a which can be at least partially inserted into the guide tips 516. The first end 554a includes a preferably axially directed (or preferably at least directed generally parallel to the longitudinal axis $A_L$ of the handle portion 552a) peg element 558a which closely corresponds in size to the inner diameter of a guide tip 516. The second end 556a is provide with four peg elements 560a, 562a, 564a, 566a, with two such pegs extending transversely to the longitudinal axis $A_L$ of the handle on each side 568a, 570a of the second end 556a. At one such side 568a, the endmost peg element 560a closely corresponds in size to the inner diameter of a guide tip 516 and the inner peg element 562a has a stepped down nipple portion 572a, whereas on the opposite side 570a of the second end the endmost peg element 564a has a stepped down nipple portion 574a stepped down in diameter and the inner peg element 566a closely corresponds in size to the interior of the guide tip 516. All the peg elements are preferably generally cylindrical, but may be polygonal or slightly tapered.

As described as follows, the benders 550a, 550b can be coupled to a fragment plate at the guide tips 516 to apply torque, lateral and longitudinal bending forces to contour the plate; i.e., to bend the plate along x-, y- and z-axes. In the present embodiment it is preferred that the benders be coupled at adjacent guide tips for localized control of plate shaping. The plate is then shaped through a series of shaping steps in which adjacent portions of the plate are sequentially shaped, as needed. Additionally all such shaping, as also discussed further below, can be performed while the plate is positioned on the bone.

Figure 16:
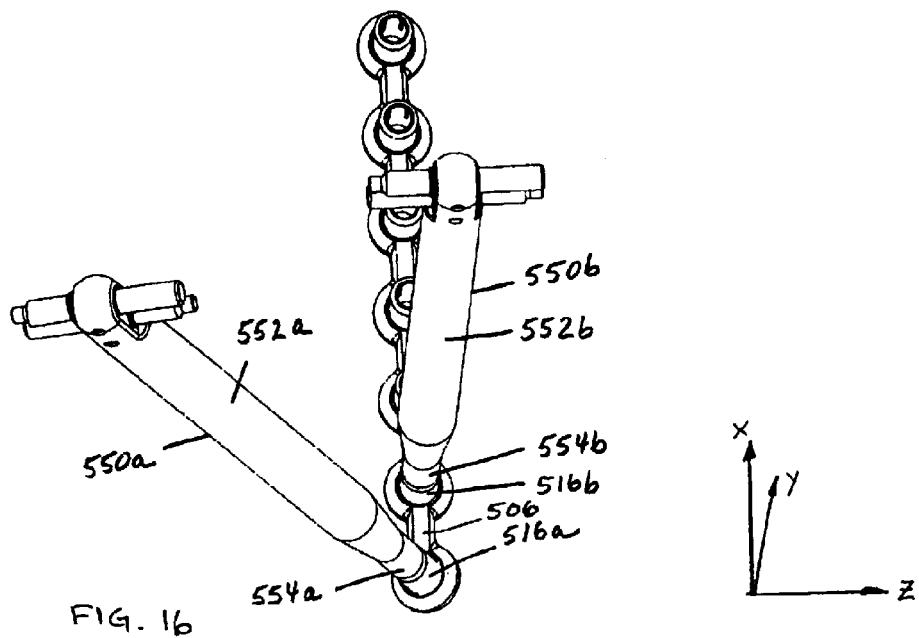
FIG. 16 is a top perspective view of the benders imparting a bend along an x-axis to impart a twist to the fragment plate along its longitudinal axis.

Referring to FIG. 16, in order to apply torque to the plate to cause the plate to twist, the peg elements 558a, 558b (FIG. 15) at the first ends 554a, 554b of the benders 550a, 550b are inserted into preferably adjacent guide tips 516a, 516b. The handle portions 552a, 552b of the benders are then forced laterally relative to each other so as to apply a torque along the bridge portion 506 of the plate between the benders. Such torque results in defining a twist in the plate without deformation to the threaded holes to bend the plate along the x-axis.

Figure 17:
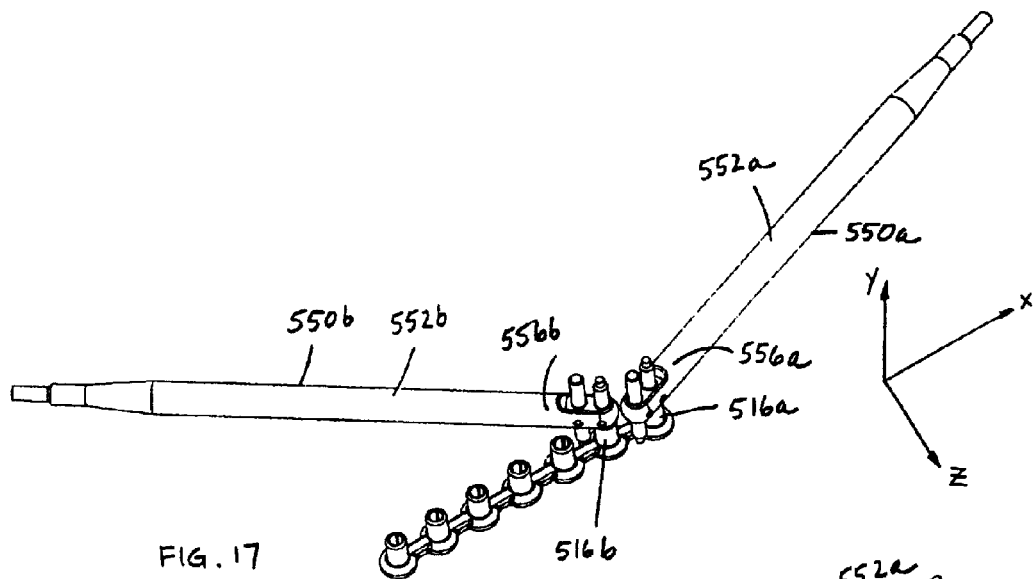
FIG. 17 is a perspective view of the benders imparting a bend along a y-axis to impart a lateral bend to the fragment plate.
Figure 18:
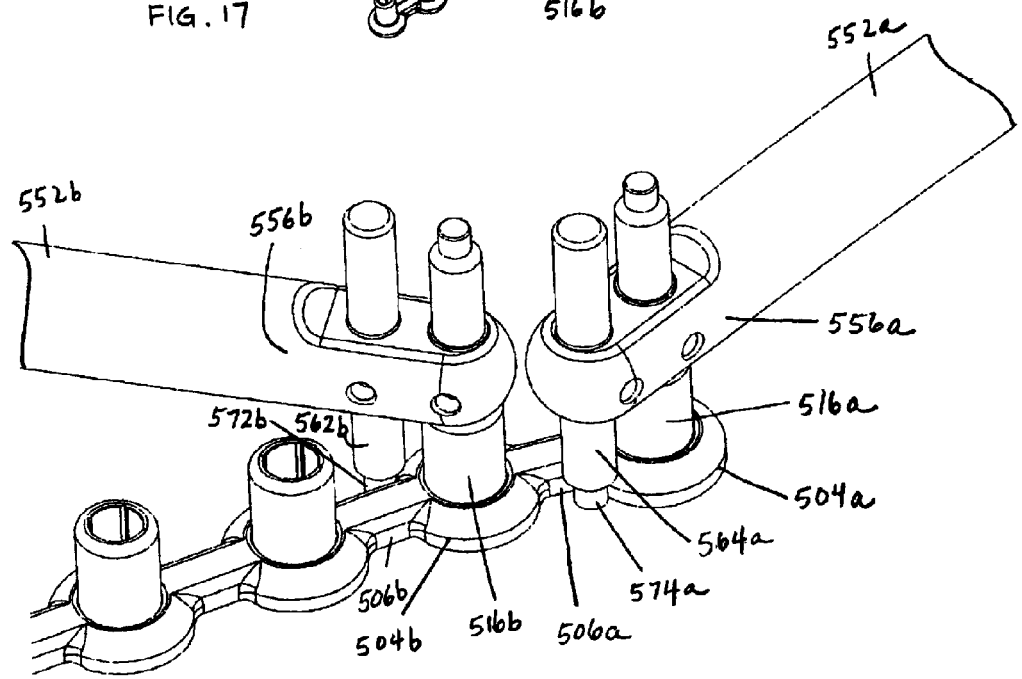
FIG. 18 is an enlarged view similar to FIG. 17.

Referring to FIGS. 17 and 18, lateral bending forces (i.e., bending within the plane of the plate) are applied with the second end 556a, 556b of the benders 550a, 550b coupled to the guide tips 516a, 516b, and then manipulating the benders to bend the plate about the y-axis. Referring to FIG. 18, more particularly, on bender 550a, peg element 566a (see FIG. 15) is inserted into guide tip 516a and the nipple portion 574a of peg element 564a functions as fulcrum (rotational stop) against the bridge portion 506a of the plate to transfer rotational forces applied by the handle portion 552a of bender 550a. On bender 550b, peg element 560b (not shown, see FIG. 15) is inserted into guide tip 516b and the nipple portion 572b of peg element 562b functions as a fulcrum (rotational stop) against the bridge portion 506b of the plate to transfer rotational forces applied by the handle portion 552b of bender 550b. As benders 550a, 550b are operated together, the resulting force subjects the plate to lateral bending at the bridge portion 506a located between the plate portions 504a, 504b at which the guide tips are coupled.

Figure 19:
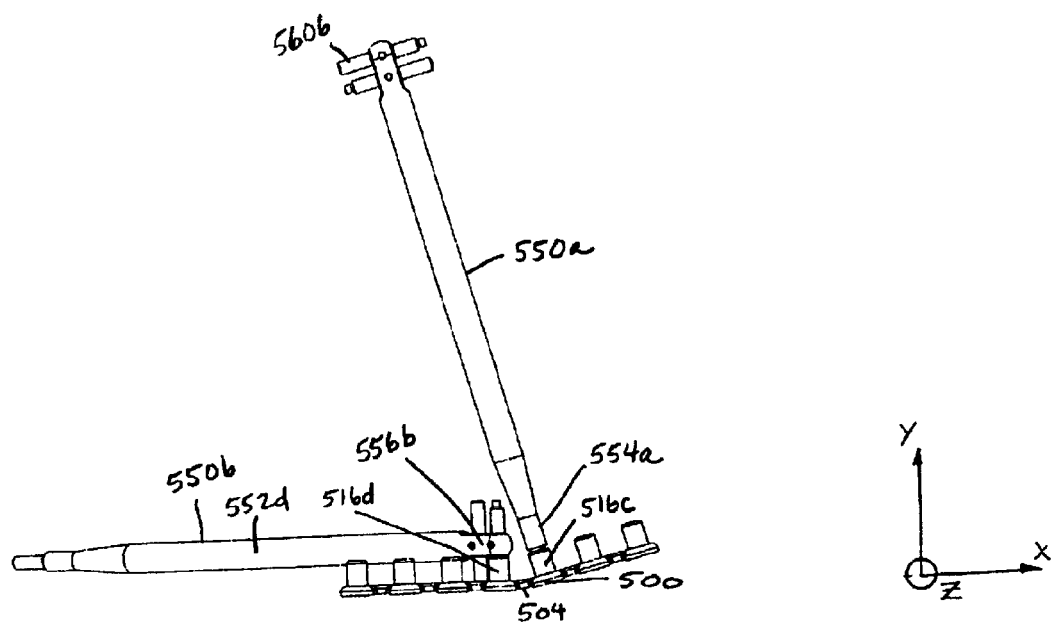
FIG. 19 is a side elevation view of the benders imparting a bend along a z-axis to impart a longitudinal bend to the fragment plate.

Referring to FIG. 19, longitudinal bending forces are applied by inserting the peg element at the first end 554a of bender 550a into guide tip 516c and a peg element, e.g. peg element 560b, at the first 554b or second ends 556b (shown) of the second bender 550b into the guide tip 516d. With the second end 556b coupled at guide tip 516d, the handle portion 552b thereof can be stabilized relative to the bone. The handle portion of tool 550a is then manipulated to bend the plate 500 at the bridge portion 504 between the two benders to bend the plate relative to the z-axis.

It is also appreciated that a single bender can be used to shape the plate once at least a portion of the plate is fixed relative to the bone. Such is described in more detail below with reference to another embodiment of a bender.

Because the benders are not coupled at any locations below the surface of the plate nor do they have any portion which would otherwise interfere with the bone or bone contacting surface, plate shaping can occur directly on the bone. In one method of operation, a hole is first drilled through a guide tip at an end of the plate. The guide tip is then removed and a threaded fastener is inserted through the threaded hole of the fragment plate and into the drilled hole to couple the plate to the bone. The benders are then worked along the plate, moving hole by hole away from the first coupled hole to shape the plate to the bone as described above. As the plate is shaped at each hole, if needed, a hole is drilled through the respective guide tip, the guide tip is removed and a threaded fastener is inserted to hold the plate to the bone. One or both of the benders are then moved to subsequent holes along the plate for shaping until the plate is fully contoured and coupled to the bone. In another method, after the plate is coupled to the bone at an end, the plate is shaped along its entire length prior to coupling to the bone at remaining holes. In yet another embodiment, the plate may be shaped to the bone before it is attached at any screw hole. It is recognized that other variations on shaping and coupling can be used.

Turning now to FIG. 20, a shapeable bone plate 600 is shown with another embodiment of the guide tips 616. The plate is substantially as described above with respect to plate 500, including an alternating arrangement of anchor and bridge portions 604, 606. Each anchor portion 604 is preferably curved along a constant radius for at least 100° adjacent its adjacent bridge portion, and more preferably approximately 120°, for cooperation with another embodiment of a plate bending tool 650a, 650b, described hereinafter.

Referring to FIGS. 20 through 22, the guide tips 616 each have a first end 618 assembled in a threaded hole in the anchor portion 604, a second end 620 extending above an outer surface 614 of the anchor portion, and a circumferentially extending shoulder 622 disposed between the first and second ends, and preferably in contact with outer surface 614 of the plate 600. The shoulder 622 doubles the load carrying capacity of the guide tips 616 relative to the prior guide tips by reducing the load carrying from the thread/thread interface and transferring load carrying to the shoulder/plate interface. The second end 620 of the guide tip 616 preferably extends no more than 0.5 inch, and more preferably is located not more than approximately 0.25 inch above the outer surface 614 of the anchor portion.

Figure 23:
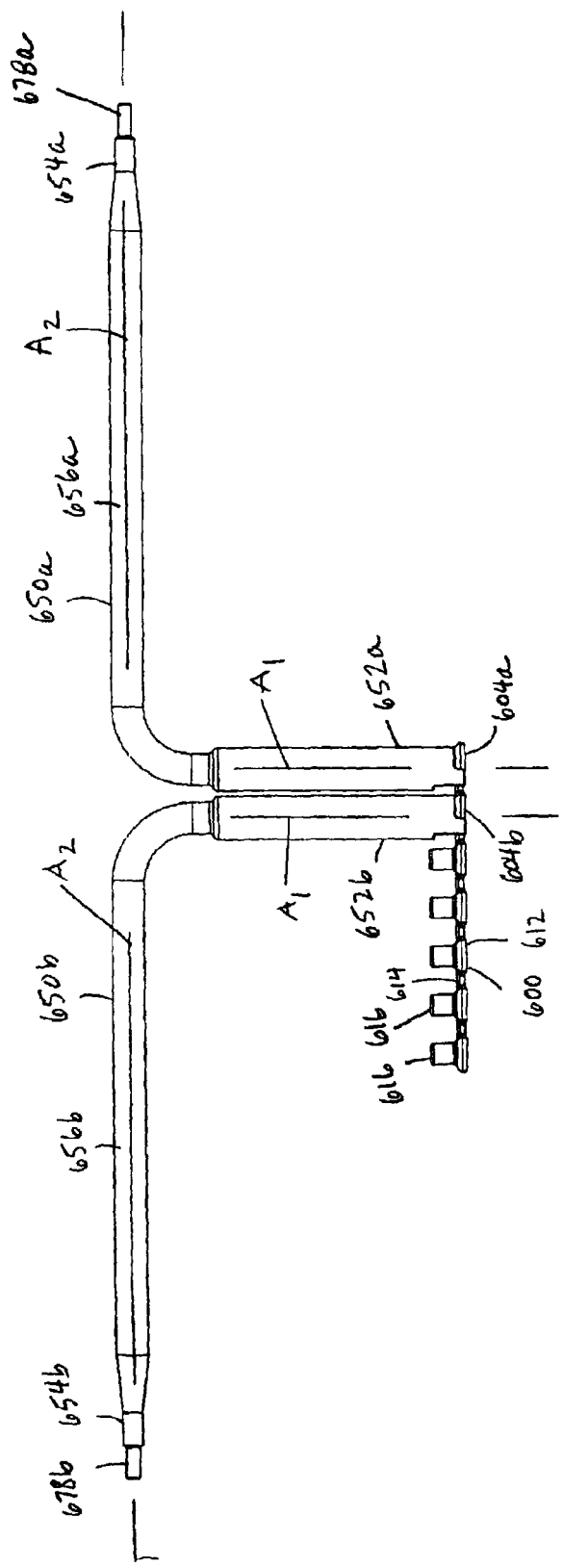
FIG. 23 is a side elevation of an assembly of FIG. 20 with another embodiment of bender.
Figure 24:
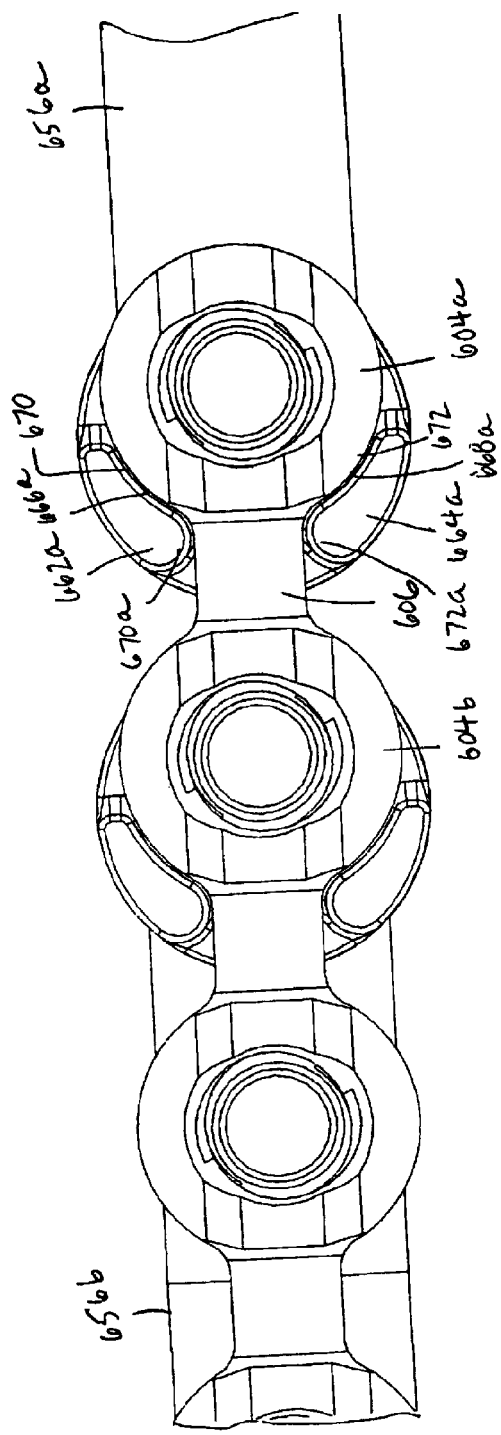
FIG. 24 is a broken bottom view of the assembly of FIG. 23.
Figure 25:
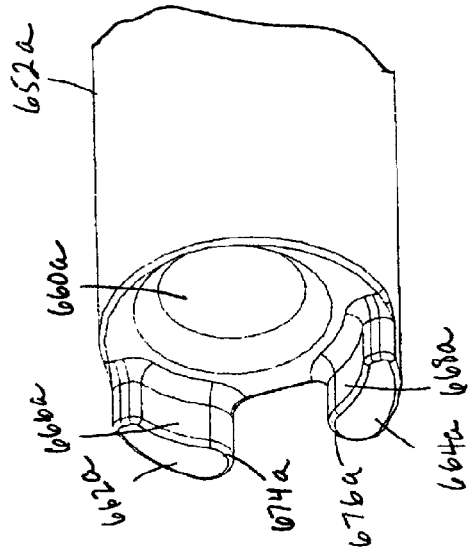
FIG. 25 is a broken bottom perspective of the bender shown in FIG. 23.

Referring to FIG. 23, a pair of plate benders 650a, 650b is shown coupled to adjacent anchor portions 604a, 604b of the plate 600. The plate benders 650a, 650b each include a first end 652a, 652b, a second end 654a, 654b, and a handle 656a, 656b extending therebetween, with the respective handles 656a, 656b preferably extending in generally opposing directions. Referring to FIGS. 23 through 25, the first end 652a defines a socket 660a sized to closely receive a guide tip 616, and means for rotationally fixing the first end 652a relative to a portion of the bone plate 600, such as the bridge portion 606. In a preferred embodiment, the means for rotationally fixing the first end relative to the bone plate are two feet 662a, 664a that straddle the bridge portion 606 of the bone plate. The two feet 662a, 664a include curved inner surfaces 666a, 668a that seat about the radiused portions 670, 672 of the anchor portion 604a to quickly and easily align the bender 656a on the plate. The feet 662a, 664a each have a toe end 674a, 676a that abuts the bridge portion 606 at an optimal location to function as a fulcrum for the bender. Referring back to FIG. 23, the second ends 654a, 654b of the benders define pegs 678a, 678b that are cylindrical and that step down in diameter from the adjacent portion of the handle. The handle 656a, 656b is preferably L-shaped and extends between the respective first and second ends. Each handle, e.g., 656a, includes a first longitudinal axis $A_1$ extending through its first end 652a and an adjacent portion of the handle and a second longitudinal axis $A_2$ extending through the second end 654a and its adjacent portion of the handle. The handle 656a is preferably bent to offset the two axes relative to each other. Most preferably, the socket 660a at the first end 652a is offset relative to the second axis $A_2$ by at least approximately 0.25 inch, more preferably at least 0.5 inch (to provide for guide tip and tissue clearance), but preferably by not more than approximately 3 inches (to maintain handle stability and control). It is noted that the benders 650a, 650b are preferably identical with the exception that the handles are bent in opposite directions from each other. The handles are coupled to the plate such that the longitudinal axis $A_1$ of each handle overlies the respective longitudinal axis of the plate portions surrounding the plate segment which is to be bent. An exception is provided at the anchor portion 604a at the end of the plate, where the appropriate bender should be coupled so that the handle extends outward from the plate, rather than over the plate.

Figure 26:
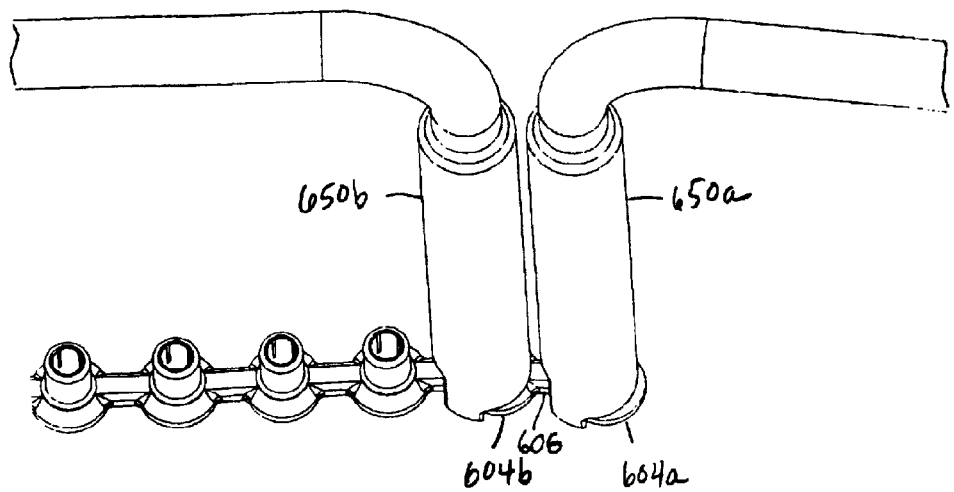
FIG. 26 is a broken perspective view of the assembly of FIG. 23, shown applying a bend along the y-axis to a bone plate.
Figure 27:
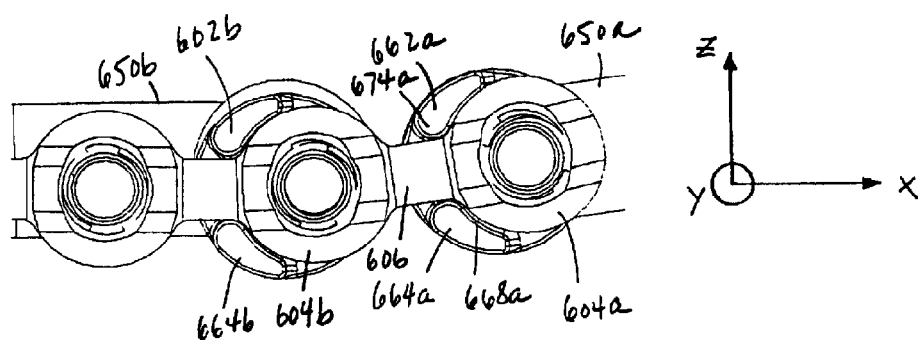
FIG. 27 is a broken bottom view showing the benders applying a bend along the y-axis to the bone plate.
Figure 28:
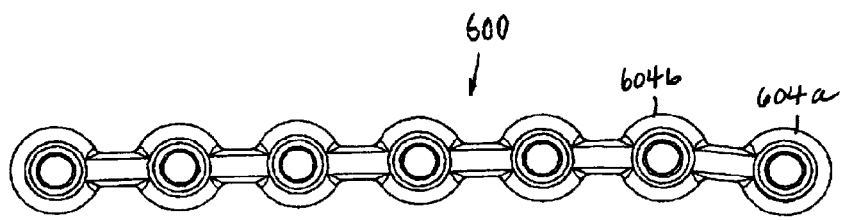
FIG. 28 is a top view of the plate with bend in the y-axis applied.

The plate 600 is generally bent so that its inner surface 612 thereof approximates the shape of the bone surface generally in the manner described above. More particularly, referring to FIGS. 26 and 27, a bend in the y-axis may be imparted to the plate at the bridge 606 between anchor portions 604a, 604b to which the benders 650a, 650b are coupled by applying a relative rotational force. In imparting such a bend, the feet 662b, 664b of bender 650b stabilize anchor 604b, while the toe 674a of foot 662a functions as a fulcrum and the inner surface 668a of the opposite foot 664a applies the force to the anchor portion 604a to impart the desired bend. Without relocating the bender, force could be applied in an opposite rotational direction and the opposite feet would perform reverse functions. Each foot also functions as a stop to limit angular displacement to approximately 40°. The 'stop' function is effected in that the toe end of the foot operating as a fulcrum contacts the adjacent anchor portion after approximately 40° of angular displacement and limits any further angular movement of the anchor portions relative to each other. FIG. 28 shows the plate 600 with a lateral bend imparted between anchor portions 604a and 604b after the benders have been removed from the plate.

Figure 29:
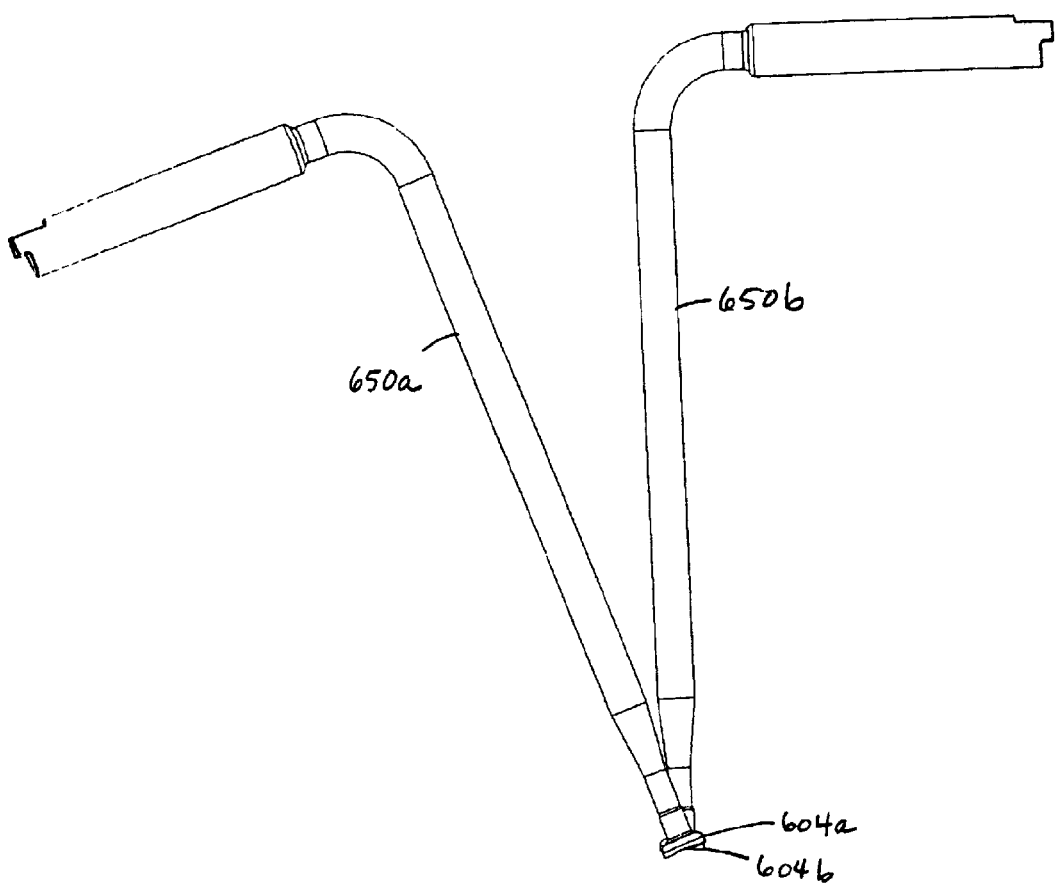
FIG. 29 is an end view of the plate, guide tip, and bender assembly, with the benders applying a bend along the x-axis to the bone plate.

In addition, the pegs 678a, 678b at the second ends of the benders can be inserted into the guide tips 616 at preferably adjacent anchor portions and can be manipulated to bend the plate relative to x- and z-axes; i.e., to impart torque and a resulting twist to the plate (x-axis displacement) and to longitudinally bend the plate up and/or down (z-axis displacement). FIG. 29 shows the benders 650a, 650b imparting a twist to the plate 600; i.e., to rotate anchor portion 604a in the x-axis relative to anchor portion 604b. It is appreciated that the benders may similarly be used to bend the plate along the z-axis.

Figure 30:
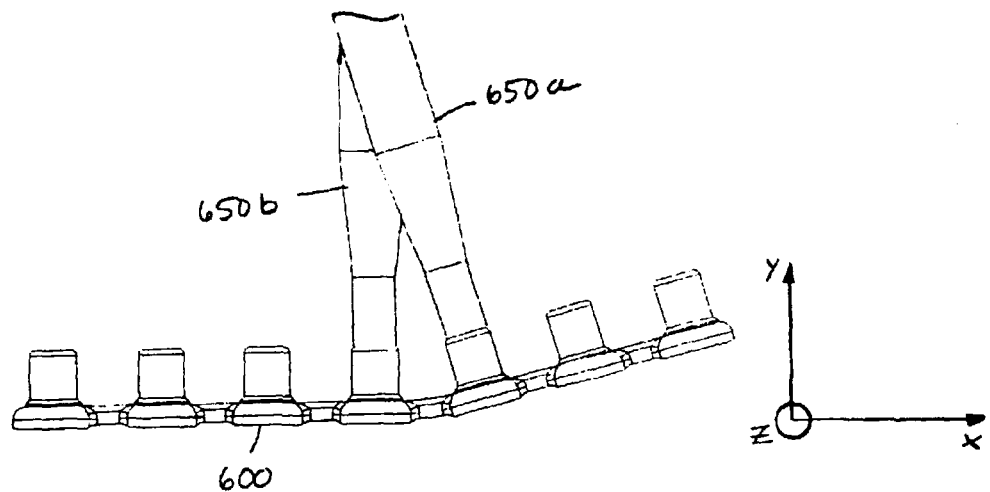
FIG. 30 is a broken side elevation of the assembly of FIG. 29 in which the benders are applying a bend along the z-axis to the bone plate.
Figure 33:
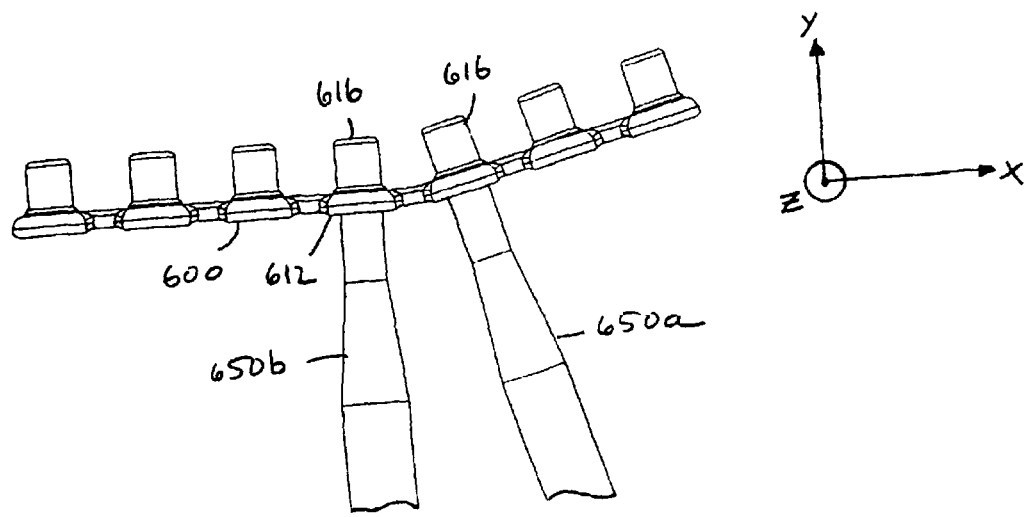
FIG. 33 is a broken side elevation of the assembly of the benders being used from the bottom of the plate to apply a bend along the z-axis to the bone plate.
Figure 31:
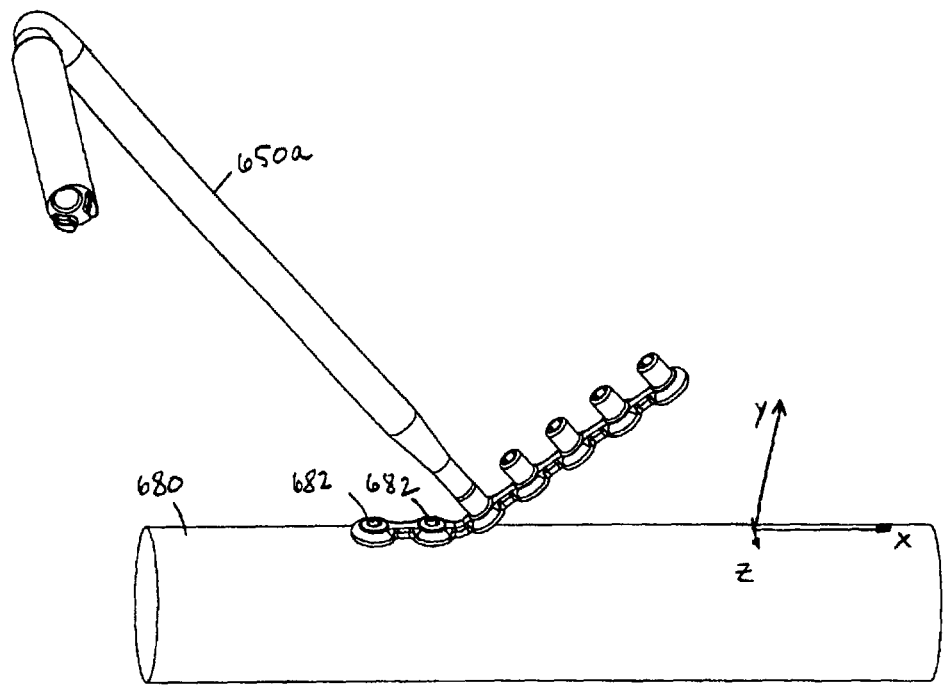
FIG. 31 shows a single bender applying a plate bend along the z-axis.
Figure 32:
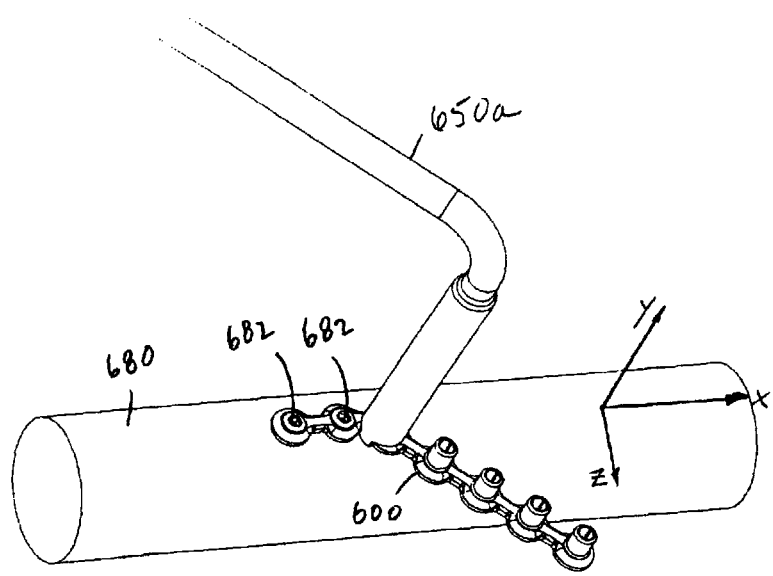
FIG. 32 shows a single bender applying a plate bend along the y-axis.

However, it is also recognized that the benders could possibly interfere with each other when the necessary z-axis bend requires moving the benders toward each other in the same plane. Referring to FIG. 30, one way to overcome any potential interference is to move the benders 650a, 650b out of plane, but this may impart an x-axis twist to the plate 600, which could be undesired. Turning to FIG. 31, one solution when working in from the end of the plate (the ends of which are already fixed to the bone 680 by screws 682) is to use a single bender 650a to impart a bend along the z-axis. Similarly, referring to FIG. 32, a bend along the x-axis can likewise be imparted. Referring to FIG. 33, another solution is to insert the pegs 678a, 678b (FIG. 23) of the benders into the guide tips 616 from the bottom 612 of the plate and then manipulate the benders 650a, 650b away from each other to effect a bend about the z-axis without any bend about the x-axis. While it is recognized that the plate cannot be coupled to the bone during this type of bending, it nevertheless may be desirable to make certain gross contour adjustments with the plate located off the bone, e.g., prior to applying the plate to the bone.

Figure 35:
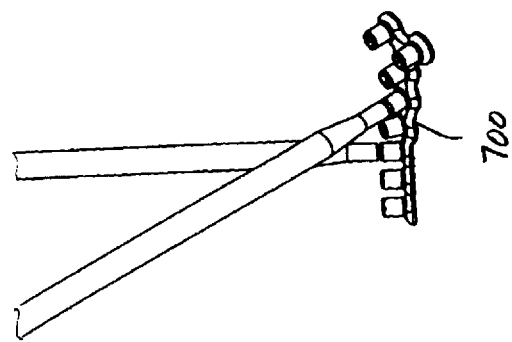
FIG. 35 is a side elevation of the assembly of FIG. 34, in which the plate is further bent along the y-axis by the benders.
Figure 34:
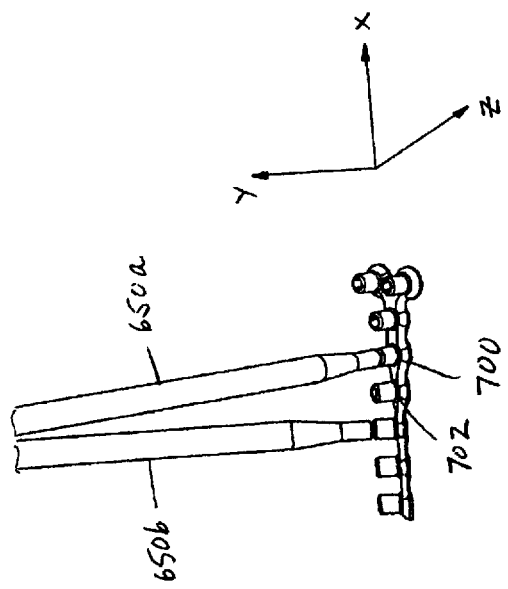
FIG. 34 is a side elevation of an assembly of another plate with guide tips, being bent along the x-axis by the benders.

In most instances, it is preferred that the bridge portion of the plate be substantially narrower than the anchor portion to facilitate bending, particularly a lateral bend along the y-axis. Nevertheless, it is appreciated that plates with smaller ratios of anchor to bridge widths can also be bent and shaped using the guide tips and tools described herein, and there are circumstances where an overall relatively stiffer plate may be desirable. For example, referring to FIGS. 34 and 35, a Y-shaped plate 700 with such a smaller ratio is shown first being torqued along the x-axis to impart a twist (FIG. 34) and then being bent along the z-axis to impart a longitudinal bend (FIG. 35) in accord with the methods described above. In such a stiffer plate 700, it is preferable to position the benders 650a, 650b in guide tips that are spaced apart by at least one threaded hole.

Figure 36:
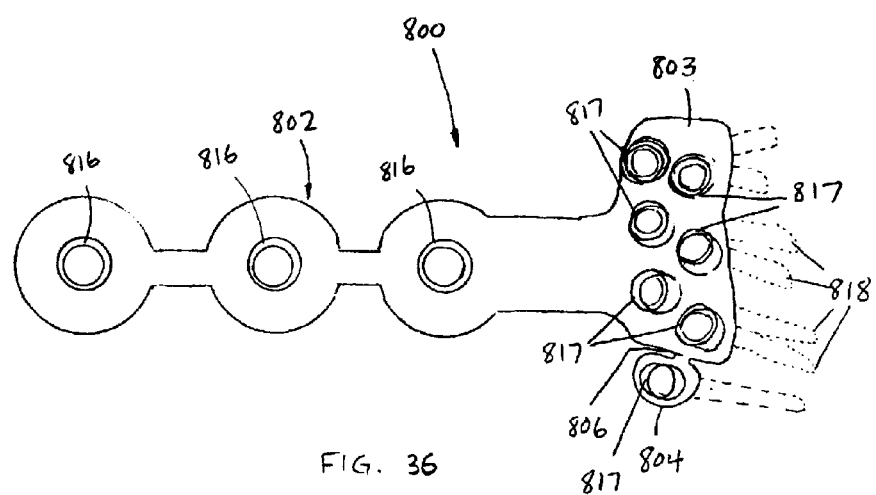
FIG. 36 is another plate according to the invention in the form of a volar T-plate.
Figure 37:
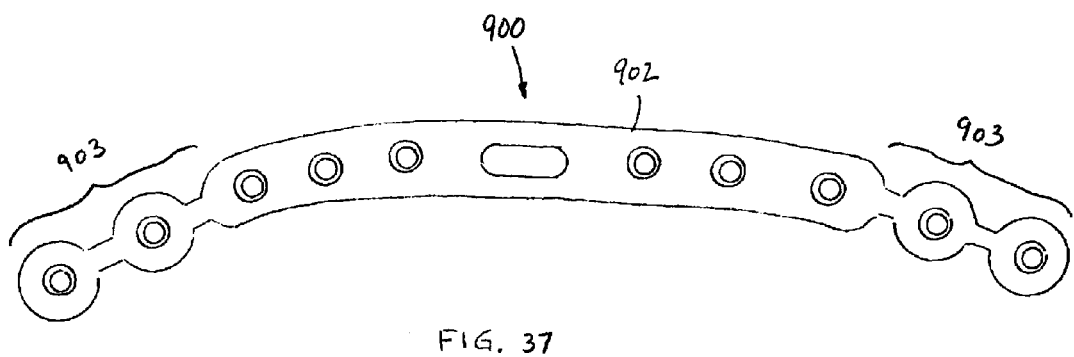
FIG. 37 is another plate according to the invention in the form of a clavicle plate.

Also, while shapeable plates described above have a construct of alternating anchor and bridge portions, it is recognized that hybrid plates may be provided that have both shapeable and relatively stiffer non-shapeable portions. Such plates are anticipated to be fracture specific and are rigid where the anatomy is relatively constant in contour across patients and shapeable where there may be individual variations in bone surface anatomy. For example, referring to FIG. 36, a volar T-plate 800 is shown in which the axial shaft portion 802 is shapeable and provided with guide tips 816. In addition, the relatively transverse head portion 803 is substantially non-shapeable, with the exception of an anchor portion 804 coupled by a bridge 806 to the remainder of the head portion 803. The anchor portion 804 is thus adapted to be shaped relative to the rest of the head portion to direct a fastener toward the volar marginal fragment. Preferably all the holes in the head portion are provided with guide tips 817. Guide tips 816 and 817 may be different sizes to accommodate relatively different diameter threaded holes in the respective portions of the plate. When the guide tips are removed from the head portion 803 and subchondral supports 818 (e.g., threaded pegs or screws) are inserted into the threaded holes therein, any load on the subchondral supports is transferred back to the axial shaft portion 802 of the plate 800. The same principal can be applied to other metaphyseal plates. By way of another example, a clavicle plate 900 is shown in FIG. 37. The clavicle plate 900 has a relatively rigid non-shapeable central portion 902, and end portions 903 that are shapeable. The same principal can be applied to other diaphyseal places.

There have been described and illustrated herein several embodiments of a bone plate with pre-assembled guide tips, benders for use with a plate with guide tips, and methods of using the same. While particular embodiments of the invention have been described, it is not intended that the invention be limited thereto, as it is intended that the invention be as broad in scope as the art will allow and that the specification be read likewise. Thus, while the tips and benders have been shown with respect to a volar plate for dorsally displaced fractures and several fragment plates, it will be appreciated that the tips may be used in conjunction with threaded holes on other bone plates as well. For example, the tips may be used in conjunction with any plate for which they would provide advantage. In addition, one or more benders may be used to customize a fracture fixation plate for other bones, e.g., the clavicle, the ulna, the olecranon, the jaw, the skull, whether such plates are pre-formed flat or contoured to fit the anatomy. Furthermore, a distal radius plate having radial and ulnar sides provided with threaded fixed angle holes, the radial and/or ulnar sides being provided with guide tips and being shapeable with the benders, is considered within the scope of the invention. Also, a distal radius plate having shapeable segment(s) for capturing a volar marginal fragment is also within the scope of the invention. Optionally, such shapeable segment(s) may be removable from the plate if not used, e.g., by repeated bending, and provide a relatively clean break with the plate. In addition, while particular engagements between the tips and the insertion/removal tool and the tips and drill guide extension have been disclosed, it will be understood that other suitable engagements, including non-destructive press-fit, snap-in, bayonet lock, etc. can also be used. Also, while the guide tips are described as threaded into the threaded holes, it is appreciated that non-threaded assemblies, including non-destructive press-fit, snap-in, bayonet lock, etc., which maintain the tips in alignment with the axes of the peg holes can also be used. While different benders have been shown, each can be used with multiple embodiments of the guide tips. With respect to the benders with multiple peg elements, preferred orientations of the peg elements have been described, but other configurations are possible within the scope of the invention. For example, the four peg elements can be located two each at, e.g., 90° apart. In addition, such benders may only have two peg elements at a second end, each with a different configuration of larger and smaller size peg elements. Furthermore, while it is preferred to work a plate for shaping by coupling the benders at guide tips at adjacent holes, it is appreciated that not all holes of a shapeable plate need be provided with a guide tip and that the benders may be used relatively more spaced apart along the plate regardless of whether all holes of a shapeable plate include guide tips. Moreover, while it is preferable that the plate be coupled to bone with bone screws while it is shaped relative to the bone, it is appreciated that the plate may be coupled to the bone with temporary fixation, such as with one or more clamps, during shaping. Furthermore, while the bendable plate segments are preferably bridge portions narrower than the surrounding anchor portions, it is appreciated that the one or more bendable segments may be of a different configuration than shown, provided that they are less rigid than the surrounding plate portions and are structured to deform prior to destruction of the plate threads in which the guide tips are threaded. It will therefore be appreciated by those skilled in the art that yet other modifications could be made to the provided invention without deviating from its scope.

What is claimed is:

1. A method of bending a bone plate, the bone plate for stabilizing a fracture of a bone, the bone plate having first and second portions, the method comprising:
   providing or obtaining a bone plating system including a bone plate having longitudinally displaced first and second threaded holes disposed therein and first and second tubular elements removably threadedly engaged in the respective first and second threaded holes;
   engaging a first and a second plate bending tool relative to the first and second tubular elements and the plate about the first and second tubular elements; and
   applying a force between the first and second plate bending tools to bend the plate between the first and second threaded holes.

2. A method according to claim 1, wherein engaging the first and second plate bending tools is carried out while the bone plate is positioned on the bone.

3. A method according to claim 1, wherein the plate includes alternating anchor portions and narrower bridge portions bridging the anchor portions, wherein the first and second threaded holes are located in each of at least two longitudinally displaced anchor portions, and the applied force of the first and second plate bending tools bends the plate between two anchor portions.

4. A method according to claim 1, wherein the plate has an upper surface, a lower bone contacting surface, and opposite sides extending between the upper and lower surfaces, and wherein each tubular guide has a fixed central axis coaxial with its respective threaded hole which is displaced between the opposite sides, and the first plate bending tool is adapted to engage the bone plate on the opposite sides.

5. A method according to claim 4, wherein the second plate bending tool is adapted to engage the plate on opposite sides of the central axis of the second threaded hole.

6. A method of bending a bone plate, the bone plate for stabilizing a fracture of a bone and having alternating anchor portions and narrower bridge portions bridging the anchor portions, at least two longitudinally displaced anchor portions each provided with a threaded hole, the method comprising:
   coupling a first plate bender about a first anchor portion, the first anchor portion having a threaded hole disposed therein and a first tubular element removably threadedly engaged in the threaded hole, the first plate bender being coupled to the first anchor portion via the first tubular element;
   coupling a second plate bender about a second anchor portion, the second anchor portion having a threaded hole disposed therein and a second tubular element removably threaded engaged in the threaded hole the second plate bender being coupled to the second anchor portion via the second tubular element; and
   applying a force relative to the first and second plate benders to bend the plate between the first and second anchor portions.

7. A method according to claim 6, wherein the threaded holes each have a respective fixed central axis extending longitudinally through a center of the threaded hole, and the first plate bender is coupled on opposite sides of the central axis of the first anchor portion.

8. A method according to claim 7, wherein the second plate bender is coupled on opposite sides of the central axis of the second anchor portion.

9. A method according to claim 6, wherein when the first plate bender is coupled about the first anchor portion, the first plate bender being not in direct contact with an interior of the threaded hole of the first anchor portion.

10. A method according to claim 9, wherein when the second plate bender is coupled about the second anchor portion, the second plate bender being not in direct contact with an interior of the threaded hole of the second anchor portion.

11. A method according to claim 6, wherein the plate is positioned on the bone while applying the force.

12. A method of bending a bone plate, the bone plate for stabilizing a fracture of a bone, the bone plate having first and second portions, the plate having a lower bone contacting surface and an opposite upper surface, the method comprising:
  a) coupling a first plate bender about the first portion of the plate, the first portion comprising a first anchor portion having a threaded hole disposed therein and a first tubular element removably threadedly coupled to the threaded hole, the first plate bender coupled to the first portion of the plate via the first tubular element, the first plate bender extending upwards from the upper surface of the plate at the first portion of the plate, not below the lower surface of the plate at the first portion, and not in direct contact with the first portion of the plate at an interior of the screw hole of the first portion of the plate;
  b) coupling a second plate bender relative to the second portion of the plate, the second portion comprising a second anchor portion having a threaded hole disposed therein and a second tubular element removably threadedly coupled to the threaded hole, the second plate bender coupled to the second portion of the plate via the second tubular element; and
  c) applying a force relative to the first and second plate benders to bend the plate between the first and second portions.

13. A method according to claim 12, wherein the bone plate has alternating anchor portions and narrower bridge portions bridging the anchor portions, each of at least two longitudinally displaced anchor portions provided with a screw hole, and the first portion is one of the anchor portions.

14. A method according to claim 12, wherein the bone plate has alternating anchor portions and narrower bridge portions bridging the anchor portions, each of at least two longitudinally displaced anchor portions provided with a screw hole, and the second portion is one of the anchor portions.

15. A method according to claim 12, wherein the second plate bender extends upwards from the upper surface of the plate at the second portion, not below the lower surface of the plate at the second portion, and not in direct contact with an interior of the screw hole of the second portion of the plate.

16. A method according to claim 12, wherein the first plate bender is coaxially coupled relative to plate such that the first plate bender is oriented coaxial with a central axis of the threaded hole of the first portion.

17. A method according to claim 12, wherein the bone plate is positioned on the bone while applying the force.

18. A method of removing a first portion of a bone plate from a second portion of the bone plate, the bone plate for stabilizing a fracture of a bone, the method comprising:
  providing or obtaining a bone plating system including a bone plate having the first and second plate portions with displaced first and second threaded holes disposed therein and first and second tubular elements removably threadedly engaged in the respective first and second threaded holes;
  engaging a first and a second plate bending tool relative to the first and second tubular elements and the plate about the first and second tubular elements; and
  applying a force between the first and second plate bending tools to bend the plate between the first and second threaded holes until the first plate portion breaks from the second plate portion.

19. A method according to claim 18, wherein the engaging the first and second plate bending tools is carried out while the bone plate is positioned on the bone.

20. A method according to claim 18, wherein the plate includes alternating anchor portions and narrower bridge portions bridging the anchor portions, wherein the first and second threaded holes are located in each of at least two longitudinally displaced anchor portions, and the applied force of the first and second plate bending tools bends the plate between two anchor portions.

21. A method according to claim 18, wherein the first plate bending tool is adapted to engage the first tubular element.

22. A method according to claim 21, wherein the plate has an upper surface, a lower bone contacting surface, and opposite sides extending between the upper and lower surfaces, and wherein each tubular guide has a fixed central axis coaxial with its respective threaded hole which is displaced between the opposite sides, and the first plate bending tool is adapted to engage the bone plate on the opposite sides.

23. A method according to claim 22, wherein the second plate bending tool is adapted to engage the plate on opposite sides of the central axis of the second threaded hole.

24. A method of removing a portion of a bone plate, the bone plate for stabilizing a fracture of a bone and having at least two anchor portions and a narrower bridge portion bridging the anchor portions, each of the at least two anchor portions provided with a threaded hole, the method comprising:
  coupling a first plate bender about a first anchor portion, the first anchor portion having a threaded hole disposed therein and a tubular element removably threadedly engaged in the threaded hole, the first plate bender being coupled to the first anchor portion via the tubular element;
  coupling a second plate bender about a second anchor portion, the second anchor portion having a threaded hole disposed therein and a tubular element removably threadedly engaged in the threaded hole, the second plate bender being coupled to the first anchor portion via the tubular element; and
  applying a force relative to the first and second plate benders to bend the plate between the first and second anchor portions to break the plate between the first and second anchor portions.

25. A method according to claim 24, wherein the first plate bender is not in direct contact with an interior of the threaded hole of the first anchor portion.

26. A method according to claim 25, wherein the second plate is not in direct contact with an interior of the threaded hole of the second anchor portion.

27. A method according to claim 24, wherein the plate is positioned on the bone while applying the force.

28. A method of removing a portion of a bone plate, the bone plate for stabilizing a fracture of a bone, the bone plate having first and second portions, each of the first and second portions having threaded screw holes, the plate having a lower bone contacting surface and an opposite upper surface, the method comprising:
  coupling a first plate bender to the first portion of the plate, the first plate bender extending upwards from the upper surface of the plate at the first portion of the plate, not below the lower surface of the plate at the first portion, and not in direct contact with an interior of the threaded screw hole of the first portion of the plate;
  using the first plate bender to apply a force between the first and second portions to bend the plate between the first and second portions until the first portion breaks off from the second portion.

29. A method according to claim 28, further comprising:
coupling a second plate bender relative to the second portion of the plate, and the first plate bender is moved relative to the second plate bender to apply the force.

30. A method according to claim 29, wherein the second plate bender extends upwards from the upper surface of the plate at the second portion, not below the lower surface of the plate at the second portion, and not in direct contact with an interior of the threaded screw hole of the second portion of the plate.

31. A method according to claim 29, wherein the bone plate is provided with tubular guides attached at the threaded screw holes, and the first and second plate benders apply a force between the tubular guides.

32. A method according to claim 28, wherein the first and second portions of the bone plate are each anchor portions and a narrower bridge portion is provided bridging the anchor portions.

33. A method according to claim 28, wherein the first portion of the bone plate is an anchor portion and a narrower bridge portion bridging the anchor portion with the second portion of the plate.

34. A method according to claim 28, wherein the first plate bender is coupled coaxially with the thread axis of the threaded hole in the first plate portion.

35. A method according to claim 28, wherein the bone plate is provided with tubular guides attached at the threaded screw holes, and the first bender applies a force to the tubular guide.

36. A method according to claim 28, wherein the bone plate is positioned on the bone while applying the force.

* * * * *

UNITED STATES PATENT AND TRADEMARK OFFICE
CERTIFICATE OF CORRECTION

PATENT NO.         : 9,615,874 B2                           Page 1 of 1
APPLICATION NO.    : 14/477321
DATED              : April 11, 2017
INVENTOR(S)        : Orbay et al.

It is certified that error appears in the above-identified patent and that said Letters Patent is hereby corrected as shown below:

In the Claims

In Column 14, Line 43, in Claim 6, after "removably", delete "threaded" and insert --threadedly-- therefor In Column 14, Line 43, in Claim 6, delete "hole" and insert --hole,-- therefor Signed and Sealed this
Twelfth Day of June, 2018

Andrei Iancu
*Director of the United States Patent and Trademark Office*